United States Patent
Tavares et al.

(10) Patent No.: US 12,049,499 B2
(45) Date of Patent: Jul. 30, 2024

(54) ANTI-CD19 ANTIBODIES AND USES THEROF

(71) Applicant: Millennium Pharmaceuticals, Inc., Cambridge, MA (US)

(72) Inventors: Daniel Tavares, Cambridge, MA (US); Bianka Prinz, Cambridge, MA (US); James Geoghegan, Cambridge, MA (US)

(73) Assignee: MILLENNIUM PHARMACEUTICALS, INC., Cambridge, MA (US)

( * ) Notice: Subject to any disclaimer, the term of this patent is extended or adjusted under 35 U.S.C. 154(b) by 107 days.

(21) Appl. No.: 17/239,010

(22) Filed: Apr. 23, 2021

(65) Prior Publication Data

US 2021/0347888 A1 Nov. 11, 2021

Related U.S. Application Data

(60) Provisional application No. 63/015,385, filed on Apr. 24, 2020.

(51) Int. Cl.
*C07K 16/28* (2006.01)

(52) U.S. Cl.
CPC .... *C07K 16/2803* (2013.01); *C07K 2317/565* (2013.01); *C07K 2317/622* (2013.01); *C07K 2317/732* (2013.01); *C07K 2317/92* (2013.01)

(58) Field of Classification Search
CPC ...................... C07K 16/2803; C07K 2317/565
USPC ........................................... 424/130.1, 133.1
See application file for complete search history.

(56) References Cited

U.S. PATENT DOCUMENTS

| | | | | |
|---|---|---|---|---|
| 9,334,331 B2* | 5/2016 | Igawa | ..................... | C07K 16/40 |
| 10,421,807 B2* | 9/2019 | Gonzales | ................ | A61P 11/00 |
| 2023/0346938 A1* | 11/2023 | Feucht | ............... | C07K 16/2803 |

FOREIGN PATENT DOCUMENTS

| | | | |
|---|---|---|---|
| WO | WO 2007/065037 A2 | 6/2007 | |
| WO | WO 2019/057100 A1 | 3/2019 | |
| WO | WO 2020/006374 A2 | 1/2020 | |
| WO | WO 2021217130 | * 10/2021 | |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Buatois V et al: "Preclinical Development of a Bispecific Antibody that Safely and Effectively Targets CD19 and CD47 for the Treatment of B-Cell Lymphoma and Leukemia", Molecular Cancer Therapeutics, vol. 17, No. 8, May 9, 2018 (May 9, 2018), pp. 1739-1751.
Herbst Ronald et al: "B-Cell Depletion in Vitro and in Vivo with an Afucosylated Anti-CD19 Antibody", Journal of Pharmacology and Experimental Therapeutics, American Society for Pharmacology and Experimental Therapeutics, US, vol. 335, No. 1, Oct. 10, 2010 (Oct. 10, 2010), pp. 213-222.
International Search Report and Written Opinion dated Jul. 21, 2021 for International Application No. PCT/US2021/028880, 20 pages.
Naddafi et al., "Anti-CD19 Monoclonal Antibodies: a New Approach to Lymphoma Therapy" International Journal of Molecular and Cellular Medicine, Summer 2015, vol. 4, No. 3, pp. 143-151.
Rudikoff S et al., "Single amino acid substitution altering antigen-binding specificity", Proceedings of the National Academy of Sciences, National Academy of Sciences, US, vol. 79, May 9, 2018 (May 9, 2018), pp. 1979-1983.
Prescribing Information for KYMRIAH (Tisagenlecleucel), May 2022 (31 pages).
Prescribing Information for YESCARTA (Axicabtagene Ciloleucel), Nov. 2022 (31 pages).

* cited by examiner

*Primary Examiner* — Lynn A Bristol
(74) *Attorney, Agent, or Firm* — PROSKAUER ROSE LLP

(57) ABSTRACT

Antibodies, fragments thereof and fusion proteins that specifically bind to CD19, are described, as well as methods of making and using such antibodies. Such antibodies, fusion proteins and fragments thereof are useful for the treatment and diagnosis of various B-cell disorders, including B-cell malignancies and autoimmune diseases.

16 Claims, 3 Drawing Sheets
Specification includes a Sequence Listing.

SEQUENCE LISTING

<160> NUMBER OF SEQ ID NOS: 46

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ser Tyr Gly Met His
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Leu Ile Trp Tyr Asp Gly Ser Asn Lys Tyr Tyr Ala Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Pro Val Glu Gly Leu Leu Arg Gly Phe Asp Tyr
1               5                   10

<210> SEQ ID NO 4
<211> LENGTH: 557
<212> TYPE: PRT
<213> ORGANISM: Homo sapiens

<400> SEQUENCE: 4

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp

```
                  115                 120                 125
Leu Gly Gly Leu Gly Cys Gly Leu Lys Asn Arg Ser Ser Glu Gly Pro
    130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Leu Pro Pro
                165                 170                 175
Arg Asp Ser Leu Asn Gln Ser Leu Ser Gln Asp Leu Thr Met Ala Pro
                180                 185                 190
Gly Ser Thr Leu Trp Leu Ser Cys Gly Val Pro Pro Asp Ser Val Ser
                195                 200                 205
Arg Gly Pro Leu Ser Trp Thr His Val His Pro Lys Gly Pro Lys Ser
                210                 215                 220
Leu Leu Ser Leu Glu Leu Lys Asp Asp Arg Pro Ala Arg Asp Met Trp
225                 230                 235                 240
Val Met Glu Thr Gly Leu Leu Leu Pro Arg Ala Thr Ala Gln Asp Ala
                245                 250                 255
Gly Lys Tyr Tyr Cys His Arg Gly Asn Leu Thr Met Ser Phe His Leu
                260                 265                 270
Glu Ile Thr Ala Arg Pro Val Leu Trp His Trp Leu Leu Arg Thr Gly
                275                 280                 285
Gly Trp Lys Val Ser Ala Val Thr Leu Ala Tyr Leu Ile Phe Cys Leu
                290                 295                 300
Cys Ser Leu Val Gly Ile Leu His Leu Gln Arg Ala Leu Val Leu Arg
305                 310                 315                 320
Arg Lys Arg Lys Arg Met Thr Asp Pro Thr Arg Arg Phe Phe Lys Val
                325                 330                 335
Thr Pro Pro Pro Gly Ser Gly Pro Gln Asn Gln Tyr Gly Asn Val Leu
                340                 345                 350
Ser Leu Pro Thr Pro Thr Ser Gly Leu Gly Arg Ala Gln Arg Trp Ala
                355                 360                 365
Ala Gly Leu Gly Gly Thr Ala Pro Ser Tyr Gly Asn Pro Ser Ser Asp
                370                 375                 380
Val Gln Ala Asp Gly Ala Leu Gly Ser Arg Ser Pro Pro Gly Val Gly
385                 390                 395                 400
Pro Glu Glu Glu Gly Glu Gly Tyr Glu Glu Pro Asp Ser Glu Glu
                405                 410                 415
Asp Ser Glu Phe Tyr Glu Asn Asp Ser Asn Leu Gly Gln Asp Gln Leu
                420                 425                 430
Ser Gln Asp Gly Ser Gly Tyr Glu Asn Pro Glu Asp Glu Pro Leu Gly
                435                 440                 445
Pro Glu Asp Glu Asp Ser Phe Ser Asn Ala Glu Ser Tyr Glu Asn Glu
                450                 455                 460
Asp Glu Glu Leu Thr Gln Pro Val Ala Arg Thr Met Asp Phe Leu Ser
465                 470                 475                 480
Pro His Gly Ser Ala Trp Asp Pro Ser Arg Glu Ala Thr Ser Leu Ala
                485                 490                 495
Gly Ser Gln Ser Tyr Glu Asp Met Arg Gly Ile Leu Tyr Ala Ala Pro
                500                 505                 510
Gln Leu Arg Ser Ile Arg Gly Gln Pro Gly Pro Asn His Glu Glu Asp
                515                 520                 525
Ala Asp Ser Tyr Glu Asn Met Asp Asn Pro Asp Gly Pro Asp Pro Ala
                530                 535                 540
```

Trp Gly Gly Gly Gly Arg Met Gly Thr Trp Ser Thr Arg
545                 550                 555

<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Glu Gly Leu Leu Arg Gly Phe Asp Tyr Trp Gly Gln
            100                 105                 110

Gly Thr Leu Val Thr Val Ser Ser
        115                 120

<210> SEQ ID NO 6
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcactg atatggtatg atggaagtaa taaatactat     180
gcagactccg tgaagggccg attcaccatc tccagagaca attccaagaa cacgctgtat     240
ctgcaaatga acagcctgag agccgaggac acggcggtgt actactgcgc caagccagtg     300
gaaggactat taagaggatt cgattactgg ggacaggta cattggtcac cgtctcctca     360

<210> SEQ ID NO 7
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ala Ser Gln Ser Val Ser Ser Ser Tyr Leu Ala
1               5                   10

```
<210> SEQ ID NO 8
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Ala Ser Gln Ser Val Arg Ser Ser Tyr Leu Ala
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Ala Ser Ser Arg Ala Thr
1               5

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Ala Ser Asn Arg Ala Thr
1               5

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Ala Ser Arg Arg Ala Thr
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Gln Ala Gly Ala Val Pro Ile Thr
1               5

<210> SEQ ID NO 13
<211> LENGTH: 10
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gln Gln Val Asp Ser Leu His Pro Phe Thr
1               5                   10

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gln Gln Ala Gly Gly Val Pro Pro Leu Thr
1               5                   10

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gln Gln Leu Phe Asp Ser Pro Tyr Thr
1               5

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Gln Ala Gly Val Pro Pro Leu Thr
1               5

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Gln Ala Gly Gly Val Pro Pro Phe Thr
1               5                   10

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 18

Gln Gln Ala Gly Val Phe Pro Phe Thr
1               5

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gln Gln Ala Gly Ile Pro Pro Tyr Thr
1               5

<210> SEQ ID NO 20
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Ala Val Pro
                85                  90                  95

Ile Thr Phe Gly Gly Gly Thr Lys Val Glu Ile Lys
            100                 105

<210> SEQ ID NO 21
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Val Asp Ser Leu His
                 85                  90                  95

Pro Phe Thr Phe Gly Gly Gly Thr Lys Val Glu Ile Lys
            100                 105
```

<210> SEQ ID NO 22
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ala Gly Gly Val Pro
                 85                  90                  95

Pro Leu Thr Phe Gly Gly Gly Thr Lys Val Glu Ile Lys
            100                 105
```

<210> SEQ ID NO 23
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Arg Ser Ser
                 20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Leu Phe Asp Ser Pro
                 85                  90                  95

Tyr Thr Phe Gly Gly Gly Thr Lys Val Glu Ile Lys
            100                 105
```

<210> SEQ ID NO 24
<211> LENGTH: 108
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Val Pro Pro
                85                  90                  95

Leu Thr Phe Gly Gly Gly Thr Lys Val Glu Ile Lys
            100                 105

<210> SEQ ID NO 25
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Gly Val Pro
                85                  90                  95

Pro Phe Thr Phe Gly Gly Gly Thr Lys Val Glu Ile Lys
            100                 105

<210> SEQ ID NO 26
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Val Phe Pro
                85                  90                  95

Phe Thr Phe Gly Gly Gly Thr Lys Val Glu Ile Lys
            100                 105

<210> SEQ ID NO 27
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Ile Pro Pro
                85                  90                  95

Tyr Thr Phe Gly Gly Gly Thr Lys Val Glu Ile Lys
            100                 105

<210> SEQ ID NO 28
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caggccggag ccgtccctat cacttttggc    300
ggagggacca aggttgagat caaa                                            324

<210> SEQ ID NO 29
<211> LENGTH: 327
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 29
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag caggtcgaca gtctccatcc tttcactttt     300
ggcggaggga ccaaggttga gatcaaa                                          327

<210> SEQ ID NO 30
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag caggccggag gcgtccctcc tctcactttt     300
ggcggaggga ccaaggttga gatcaaa                                          327

<210> SEQ ID NO 31
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
gaaattgtgt tgacgcagtc tccaggcacc ctgtctttgt ctccagggga aagagccacc      60
ctctcctgca gggccagtca gagtgttagg agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagctcttcg acagtcctta cactttggc     300 ggagggacca aggttgagat caaa                                             324

<210> SEQ ID NO 32
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
gaaattgtgt tgacgcagtc tccaggcacc ctgtctttgt ctccagggga aagagccacc      60
```

```
ctctcctgca gggccagtca gagtgttagg agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caggccggag tccccctct cacttttggc     300 ggagggacca aggttgagat caaa                                           324
```

<210> SEQ ID NO 33
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

```
gaaattgtga tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caggccggag gcgtccctcc tttcactttt     300
ggcggaggga ccaaggttga gatcaaa                                        327
```

<210> SEQ ID NO 34
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34

```
gaaattgtga tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca acagggccac tggcatccca    180
gacaggttca gtggcagtgg gtctgggaca gacttcactc tcaccatcag cagactggag    240
cctgaagatt ttgcagtgta ttactgtcag caggccggag tcttcccttt cacttttggc     300
ggagggacca aggttgagat caaa                                           324
```

<210> SEQ ID NO 35
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35

```
gaaattgtgt tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca gaagggccac tggcatccca    180
gacaggttca gtggcagtgg gtctgggaca gacttcactc tcaccatcag cagactggag    240
```

```
cctgaagatt ttgcagtgta ttactgtcag caggccggca tccccccctta cactttttggc    300 ggagggacca aggttgagat caaa                                             324
```

<210> SEQ ID NO 36
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

```
Gly Gly Gly Gly Ser Gly Gly Gly Gly Ser Gly Gly Gly Gly Ser
1               5                   10                  15
```

<210> SEQ ID NO 37
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

```
Gly Gly Gly Gly Ser Gly Gly Gly Gly Ser Gly Gly Gly Ser Gly Gly
1               5                   10                  15

Gly Gly Ser
```

<210> SEQ ID NO 38
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

```
Gly Gly Gly Gly Ser Gly Gly Gly Gly Ser Gly Gly Gly Gly Ser Gly
1               5                   10                  15

Gly Gly Ser Gly Gly Gly Gly Ser
            20
```

<210> SEQ ID NO 39
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

```
Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Gly Ser
            20                  25
```

<210> SEQ ID NO 40
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Met Asp Met Arg Val Pro Ala Gln Leu Leu Gly Leu Leu Leu Leu Trp
1               5                   10                  15

Leu Pro Asp Thr Arg Cys
            20

<210> SEQ ID NO 41
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Met Glu Phe Gly Leu Ser Trp Val Phe Leu Val Ala Leu Leu Arg Gly
1               5                   10                  15

Val Gln Cys

<210> SEQ ID NO 42
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Ala Val Pro
                85                  90                  95

Ile Thr Phe Gly Gly Gly Thr Lys Val Glu Ile Lys Gly Gly Gly Gly
            100                 105                 110

Ser Gly Gly Gly Gly Ser Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Leu Ile Trp Tyr
                165                 170                 175

Asp Gly Ser Asn Lys Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

```
Leu Arg Ala Glu Asp Thr Ala Val Tyr Tyr Cys Ala Lys Pro Val Glu
    210                 215                 220

Gly Leu Leu Arg Gly Phe Asp Tyr Trp Gly Gln Gly Thr Leu Val Thr
225                 230                 235                 240

Val Ser Ser

<210> SEQ ID NO 43
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Phe Asp Ser Pro
                85                  90                  95

Tyr Thr Phe Gly Gly Gly Thr Lys Val Glu Ile Lys Gly Gly Gly Gly
            100                 105                 110

Ser Gly Gly Gly Gly Ser Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Leu Ile Trp Tyr
                165                 170                 175

Asp Gly Ser Asn Lys Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Ala Lys Pro Val Glu
    210                 215                 220

Gly Leu Leu Arg Gly Phe Asp Tyr Trp Gly Gln Gly Thr Leu Val Thr
225                 230                 235                 240

Val Ser Ser

<210> SEQ ID NO 44
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44
```

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Glu Gly Leu Leu Arg Gly Phe Asp Tyr Trp Gly Gln
            100                 105                 110

Gly Thr Leu Val Thr Val Ser Gly Gly Gly Ser Gly Gly
            115                 120                 125

Gly Ser Gly Gly Gly Ser Glu Ile Val Leu Thr Gln Ser Pro Gly
        130                 135                 140

Thr Leu Ser Leu Ser Pro Gly Glu Arg Ala Thr Leu Ser Cys Arg Ala
145                 150                 155                 160

Ser Gln Ser Val Ser Ser Ser Tyr Leu Ala Trp Tyr Gln Gln Lys Pro
                165                 170                 175

Gly Gln Ala Pro Arg Leu Leu Ile Tyr Gly Ala Ser Arg Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln Ala Gly Ile Pro Pro Tyr Thr Phe Gly Gly Thr Lys Val
225                 230                 235                 240

Glu Ile Lys

<210> SEQ ID NO 45
<211> LENGTH: 556
<212> TYPE: PRT
<213> ORGANISM: Homo sapiens

<400> SEQUENCE: 45

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

```
Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
530                 535                 540

Gly Gly Gly Gly Arg Met Gly Thr Trp Ser Thr Arg
```

```
<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Gly Gly Gly Ser
1               5
```

ANTI-CD19 ANTIBODIES AND USES THEROF

CROSS REFERENCE TO RELATED APPLICATIONS

This application claims priority to U.S. Provisional Patent Application Ser. No. 60/015,385 filed Apr. 24, 2020, the entirety of which is hereby incorporated by reference.

PARTIES TO A JOINT RESEARCH AGREEMENT

The instant application was made by or on behalf of a party to a joint research agreement. The parties to the joint research agreement are Millennium Pharmaceuticals Inc. and Memorial Sloan-Kettering Cancer Center.

SEQUENCE LISTING

The instant application contains a Sequence Listing which has been submitted electronically in ASCII format and is hereby incorporated by reference in its entirety. Said ASCII copy, created on Mar. 30, 2021, is named MIL-004US1_SL.txt and is 38,765 bytes in size.

BACKGROUND

CD19 antigen is a cell surface protein found on B cells. CD19 is expressed on both normal B cells and malignant B cells, whose abnormal growth can lead to B-cell lymphomas. For example, CD19 is expressed on B-cell lineage malignancies, including, but not limited to, non-Hodgkin's lymphoma, chronic lymphocytic leukaemia, and acute lymphoblastic leukaemia. There is a need in the art for developing anti-CD19 antibodies.

SUMMARY OF INVENTION

To address the many issues related to B-cell disorders and their treatment, the present invention provides human anti-CD19 antibodies and fragments thereof, for the treatment of B cell lymphomas and leukemias and autoimmune disorders. The antibodies and fragments thereof of the present invention can be used alone, in fusion proteins or conjugated to at least one diagnostic and/or therapeutic agent or in combination with other treatment modalities. Binding of human CD19 with the anti-CD19 antibodies or fragments thereof described herein may demonstrate ADCC activity, induction of apoptosis and inhibition of B cell proliferation.

In one aspect, the present invention provides an antibody or fragment thereof that specifically binds to CD19. In one aspect, the present invention provides a CD19 antibody or fragment thereof comprising a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGAVPIT (SEQ ID NO: 12) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQVDSLHPFT (SEQ ID NO: 13) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPLT (SEQ ID NO: 14) (LCDR3).

In some embodiments, the CD19 antibody or fragment thereof further comprises a light chain variable region with complementarity determining region (CDR) sequences of RASQSVRSSYLA (SEQ ID NO: 8) (LCDR1), GASSRAT (SEQ ID NO: 9) (LCDR2), and QQLFDSPYT (SEQ ID NO: 15) (LCDR3).

In some embodiments, the CD19 antibody or fragment thereof further comprises a light chain variable region with complementarity determining region (CDR) sequences of RASQSVRSSYLA (SEQ ID NO: 8) (LCDR1), GASSRAT (SEQ ID NO: 9) (LCDR2), and QQAGVPPLT (SEQ ID NO: 16) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPFT (SEQ ID NO: 17) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASNRAT (SEQ ID NO: 10) (LCDR2), and QQAGVFPFT (SEQ ID NO: 18) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASRRAT (SEQ ID NO: 11) (LCDR2), and QQAGIPPYT (SEQ ID NO: 19) (LCDR3).

In some embodiments, the CD19 antibody or fragment thereof comprises an immunoglobulin light chain variable (VL) region comprising an amino acid sequence that is at least 90% identical to SEQ ID NO: 20; and an immunoglobulin heavy chain variable (VH) region comprising an amino acid sequence that is at least 90% identical to SEQ ID NO: 5.

In one aspect, the present invention provides a CD19 antibody or fragment thereof comprising an immunoglobulin light chain variable (VL) region comprising an amino acid sequence that is at least 90% identical to SEQ ID NOs: 20-27; and an immunoglobulin heavy chain variable (VH) region comprising an amino acid sequence that is at least 90% identical to SEQ ID NO: 5.

In some embodiments, the VL region comprises an amino acid sequence that is at least 95% identical to SEQ ID NOs: 20-27.

In some embodiments, the VL region comprises an amino acid sequence that is identical to SEQ ID NOs: 20-27.

In some embodiments, the VH region comprises an amino acid sequence that is at least 95% identical to SEQ ID NO: 5.

In some embodiments, the VH region comprises an amino acid sequence that is identical to SEQ ID NO: 5.

In some embodiments, the VL region comprises an amino acid sequence that is identical to SEQ ID NOs:20-27 and the VH region is identical to SEQ ID NO: 5.

In some embodiments, the CD19 antibody or fragment thereof is selected from the group consisting of an IgA antibody, IgG antibody, IgE antibody, IgM antibody, bi- or multi-specific antibody, Fab fragment, Fab' fragment, F(ab')2 fragment, Fd' fragment, Fd fragment, isolated CDRs or sets thereof; single-chain variable fragment (scFv), polypeptide-Fc fusion, single domain antibody, cameloid antibody; masked antibody, Small Modular ImmunoPharmaceutical ("SMIPs™"), single chain, Tandem diabody, VHHs, Anticalin, Nanobody, minibodies, BiTE®, ankyrin repeat protein, DARPIN, Avimer, DART®, TCR-like antibody, Adnectin, Affilin®, Trans-body; Affibody, TrimerX, Micro-Protein, Fynomer, Centyrin; and KALBITOR®.

In some embodiments, the CD19 antibody or fragment thereof is a monoclonal antibody or a single-chain variable fragment (scFv).

In some embodiments, the CD19 antibody or fragment thereof is an antibody comprising an IgG constant region.

In some embodiments, the CD19 antibody or fragment thereof is a single-chain variable fragment (scFv).

In some embodiments, the CD19 scFv comprises linker sequence comprising SEQ ID Nos: 36-39.

In some embodiments, the CD19 scFv comprises a signal peptide selected from SEQ ID NOs: 40-42.

In some embodiments, the antibody or fragment thereof binds CD19 with a KD between about 8 nanomolar (nM) and about 242 nM.

In some embodiments, the antibody or fragment thereof binds CD19 on target cells with an EC50 between about 0.1 nM and about 2.7 nM.

In one aspect, the present invention provides a method of treating a cancer comprising administering the CD19 antibody or fragment thereof of any one of the preceding claims to a subject in need of treatment.

In some embodiments, the cancer is selected from leukemia, lymphoma, or myeloma.

In one aspect, the present invention provides a pharmaceutical composition comprising a CD19 antibody or fragment thereof and a pharmaceutically acceptable carrier, wherein the CD19 antibody or fragment thereof comprises a heavy chain variable region with complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGAVPIT (SEQ ID NO: 12) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQVDSLHPFT (SEQ ID NO: 13) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPLT (SEQ ID NO: 14) (LCDR3).

In some embodiments, the CD19 antibody or fragment thereof further comprises a light chain variable region with complementarity determining region (CDR) sequences of RASQSVRSSYLA (SEQ ID NO: 8) (LCDR1), GASSRAT (SEQ ID NO: 9) (LCDR2), and QQLFDSPYT (SEQ ID NO: 15) (LCDR3).

In some embodiments, the CD19 antibody or fragment thereof further comprises a light chain variable region with complementarity determining region (CDR) sequences of RASQSVRSSYLA (SEQ ID NO: 8) (LCDR1), GASSRAT (SEQ ID NO: 9) (LCDR2), and QQAGVPPLT (SEQ ID NO: 16) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPFT (SEQ ID NO: 17) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASNRAT (SEQ ID NO: 10) (LCDR2), and QQAGVFPFT (SEQ ID NO: 18) (LCDR3).

In some embodiments, the CD19 antibody or fragment thereof further comprises a light chain variable region with complementarity determining region (CDR) sequences of RASQSVSSSYLA (SEQ ID NO: 7) (LCDR1), GASRRAT (SEQ ID NO: 11) (LCDR2), and QQAGIPPYT (SEQ ID NO: 19) (LCDR3).

In one aspect, the present invention provides a method of treating a cancer comprising administering an CD19 antibody or fragment thereof to a subject in need of treatment, wherein the CD19 antibody or fragment thereof comprises a heavy chain variable region with complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3).

In some embodiments, the method of treating a cancer comprises administering a CD19 antibody or fragment thereof that further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGAVPIT (SEQ ID NO: 12) (LCDR3).

In some embodiments, the method of treating a cancer comprises administering a CD19 antibody or fragment thereof that further comprises a light chain variable region with complementarity determining region (CDR) sequences of RASQSVSSSYLA (SEQ ID NO: 7) (LCDR1), GASSRAT (SEQ ID NO: 9) (LCDR2), and QQVDSLHPFT (SEQ ID NO: 13) (LCDR3).

In some embodiments, the method of treating a cancer comprises administering a CD19 antibody or fragment thereof that further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPLT (SEQ ID NO: 14) (LCDR3).

In some embodiments, the method of treating a cancer comprises administering a CD19 antibody or fragment thereof that further comprises a light chain variable region with complementarity determining region (CDR) sequences of RASQSVRSSYLA (SEQ ID NO: 8) (LCDR1), GASSRAT (SEQ ID NO: 9) (LCDR2), and QQLFDSPYT (SEQ ID NO: 15) (LCDR3).

In some embodiments, the method of treating a cancer comprises administering a CD19 antibody or fragment thereof that further comprises a light chain variable region with complementarity determining region (CDR) sequences of RASQSVRSSYLA (SEQ ID NO: 8) (LCDR1), GASSRAT (SEQ ID NO: 9) (LCDR2), and QQAGVPPLT (SEQ ID NO: 16) (LCDR3).

In some embodiments, the method of treating a cancer comprises administering a CD19 antibody or fragment thereof that further comprises a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPFT (SEQ ID NO: 17) (LCDR3).

In some embodiments, the method of treating a cancer comprises administering a CD19 antibody or fragment thereof that further comprises a light chain variable region with complementarity determining region (CDR) sequences of RASQSVSSSYLA (SEQ ID NO: 7) (LCDR1), GASNRAT (SEQ ID NO: 10) (LCDR2), and QQAGVFPFT (SEQ ID NO: 18) (LCDR3).

In some embodiments, the method of treating a cancer comprises administering a CD19 antibody or fragment thereof that further comprises a light chain variable region with complementarity determining region (CDR) sequences of RASQSVSSSYLA (SEQ ID NO: 7) (LCDR1), GASRRAT (SEQ ID NO: 11) (LCDR2), and QQAGIPPYT (SEQ ID NO: 19) (LCDR3).

In one aspect, the present invention provides a nucleic acid encoding an amino acid sequence that is at least 90% identical to SEQ ID NO: 5.

In one aspect, the present invention provides a nucleic acid encoding an amino acid sequence that is at least 90% identical to any one of SEQ ID NOs:20-27.

In one aspect, the present invention provides a vector comprising an nucleic acid sequence of encoding an amino acid sequence that is at least 90% identical to SEQ ID NO: 5 and/or encoding an amino acid sequence that is at least 90% identical to any one of SEQ ID NOs:20-27.

In one aspect, the present invention provides an isolated cell comprising a vector comprising an nucleic acid sequence of encoding an amino acid sequence that is at least 90% identical to SEQ ID NO: 5 and/or encoding an amino acid sequence that is at least 90% identical to any one of SEQ ID NOs: 20-27.

Definitions

A or An: The articles "a" and "an" are used herein to refer to one or to more than one (i.e., to at least one) of the grammatical object of the article. By way of example, "an element" means one element or more than one element.

Affinity: As used herein, the term "affinity" refers to the characteristics of a binding interaction between a binding moiety (e.g., an antigen binding moiety (e.g., variable domain described herein) and/or Fc receptor binding moiety (e.g., FcRn binding moiety described herein)) and a target (e.g., an antigen (e.g., CD19) and/or FcR (e.g., FcRn)) and that indicates the strength of the binding interaction. In some embodiments, the measure of affinity is expressed as a dissociation constant ($K_D$). In some embodiments, a binding moiety has a high affinity for a target (e.g., a $K_D$ of less than about $10^{-7}$ M, less than about $10^{-8}$ M, or less than about $10^{-9}$ M). In some embodiments, a binding moiety has a low affinity for a target (e.g., a $K_D$ of higher than about $10^{-7}$ M, higher than about $10^{-6}$ M, higher than about $10^{-5}$ M, or higher than about 10-+M). In some embodiments, a binding moiety has high affinity for a target at a first pH, has low affinity for the target at a second pH, and has an intermediate affinity for the target at a pH level between the first pH and the second pH.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')2, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

Binding Moiety: As used herein, a "binding moiety" is any molecule or part of a molecule capable of specifically binding a target, e.g., a target of interest (e.g., an antigen (e.g., CD19) and/or FcR (e.g., FcRn)). Binding moieties include, e.g., antibodies, antigen binding fragments thereof, Fc regions or Fc fragments thereof, antibody mimetics, peptides, and aptamers.

Antigen-binding fragment or antigen fragment thereof refers to a portion of an intact antibody. An antigen-binding fragment or antibody fragment thereof refers to a portion of an intact antibody that binds to an antigen (e.g., CD19). An antigen-binding fragment can contain the antigenic determining variable regions of an intact antibody. Examples of antibody fragments include, but are not limited to Fab, Fab', F(ab')2, and Fv fragments, linear antibodies, antibody mimetics, scFvs, and single chain antibodies.

Complementarity Determining Region (CDR): A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283: 1 156-1166, 2008.

Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

Constant region: As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

Epitope: As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al, (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software known in the art, e.g., Refmac and Phenix. Mutagenesis mapping studies may be accomplished using any method known to one of skill in the art. See, e.g., Champe M et al, (1995) J Biol Chem 270: 1388-1394 and Cunningham B C & Wells J A (1989) Science 244: 1081-1085 for a description of mutagenesis techniques, including alanine scanning mutagenesis techniques.

Fc region: As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

$K_a$: As used herein, "$K_a$" refers to an association rate of a particular binding moiety and a target to form a binding moiety/target complex.

$K_d$: As used herein, "$K_d$" refers to a dissociation rate of a particular binding moiety/target complex.

$K_D$: As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

Reference: A "reference" entity, system, amount, set of conditions, etc., is one against which a test entity, system, amount, set of conditions, etc. is compared as described herein. For example, in some embodiments, a "reference" antibody is a control antibody that is not engineered as described herein.

Selective binding: As used herein, "selective binding", "selectively binds" "specific binding", or "specifically binds" refers, with respect to a binding moiety and a target, preferential association of a binding moiety to a target and not to an entity that is not the target. A certain degree of non-specific binding may occur between a binding moiety and a non-target. In some embodiments, a binding moiety selectively binds a target if binding between the binding moiety and the target is greater than 2-fold, greater than 5-fold, greater than 10-fold, or greater than 100-fold as compared with binding of the binding moiety and a non-target. In some embodiments, a binding moiety selectively binds a target if the binding affinity is less than about $10^{-5}$ M, less than about $10^{-6}$ M, less than about $10^{-7}$ M, less than about $10^{-8}$ M, or less than about $10^{-9}$ M. In some embodiments, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art.

Single-chain variable fragment (scFv): As used herein, the term "single-chain variable fragment" or "scFv" refers to a fusion protein of the variable regions of the heavy ($V_H$) and light chains ($V_L$) of an immunoglobulin (e.g., mouse or human) covalently linked to form a $V_H$:: $V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910$^{-1917}$ (2008) and WO 2014/087010, the contents of which are hereby incorporated by reference in their entireties.

Subject: The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

Target: As used herein, a "target" is any molecule specifically bound by a binding moiety of an antibody or an antigen-binding fragment thereof. In some embodiments, a target is an antigen described herein (e.g., CD19). In some embodiments, a target is an FcR (e.g., FcRn). The terms "first target" and "second target" are used herein to refer to molecules of two distinct molecular species, rather than two molecules of the same molecular species. For example, in some embodiments, a first target is a serum protein and a second target is FcRn.

Therapeutically effective amount: As used herein, the term "therapeutically effective amount" refers to an amount of a therapeutic molecule (e.g., an anti-CD19 antibody described herein) which confers a therapeutic effect on a treated subject, at a reasonable benefit/risk ratio applicable to any medical treatment. Therapeutic effect may be objective (i.e., measurable by some test or marker) or subjective (i.e., subject gives an indication of or feels an effect). In particular, the "therapeutically effective amount" refers to an amount of a therapeutic molecule or composition effective to treat, ameliorate, or prevent a particular disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount can be administered in a dosing regimen that may comprise multiple unit doses. For any particular therapeutic molecule, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific therapeutic molecule employed; the duration of the treatment; and like factors as is well known in the medical arts.

Treatment: As used herein, the term "treatment" (also "treat" or "treating") refers to any administration of a therapeutic molecule (e.g., an anti-CD19 antibody described herein) that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

BRIEF DESCRIPTION OF DRAWINGS

Drawings are for illustration purposes only; not for limitation.

DETAILED DESCRIPTION

Figure 1:
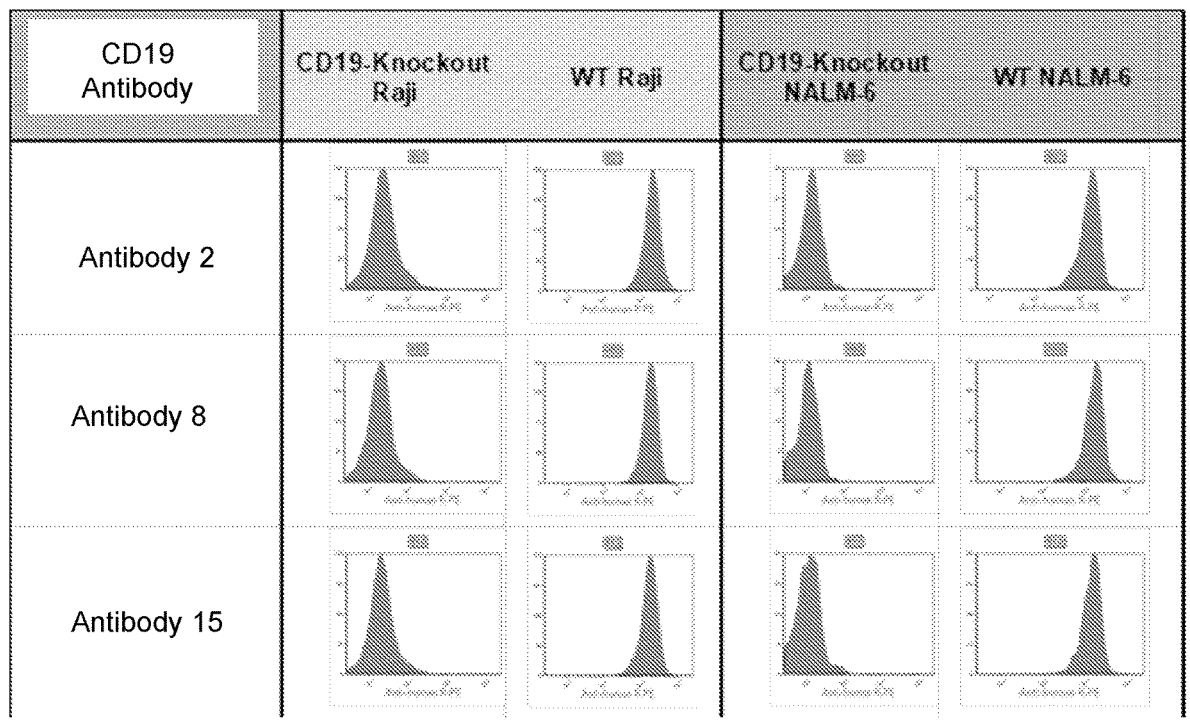
FIG. 1 shows exemplary flow cytometry chromatograms of anti-CD19 antibodies binding to CD19 expressing Raji and NALM-6 cells wild type and CD19 knockout.

The present disclosure is based, in part, on the discovery of engineered antibodies and antigen binding fragments thereof that exhibit binding to CD19 (e.g., human CD19). CD19 (also known as Cluster of Differentiation 19, B-lymphocyte antigen CD19, B-lymphocyte surface antigen B4, B4, CVID3, or Differentiation antigen CD19) is a protein with a single transmembrane domain, a cytoplasmic C-terminus, and extracellular N-terminus. CD19 is specifically expressed in normal and neoplastic B cells, as well as follicular dendritic cells. The surface density of CD19 is highly regulated throughout B cell development and maturation until the loss of expression during terminal plasma cell differentiation. In addition, CD19 is a surface biomarker for B lymphocytes and therefore may be a useful antigen for recognizing cancer cells that arise from this type of B cell, (e.g., B-cell lymphomas).

Antibodies

Anti-CD19 antibodies described herein are designed to specifically bind to CD19. In certain embodiments, the presently disclosed anti-CD19 antibodies and fragments thereof bind to human CD19. In certain embodiments, the human CD19 comprises or consists of the amino acid sequence with a NCBI Reference No: NP_001171569.1 (SEQ ID NO: 4), or a fragment thereof.

SEQ ID NO: 4 is provided below:

```
                                            [SEQ ID NO: 4]
MPPPRLLFFL LFLTPMEVRP EEPLVVKVEE GDNAVLQCLK

GTSDGPTQQL TWSRESPLKP FLKLSLGLPG LGIHMRPLAI

WLFIFNVSQQ MGGFYLCQPG PPSEKAWQPG WTVNVEGSGE

LFRWNVSDLG GLGCGLKNRS SEGPSSPSGK LMSPKLYVWA

KDRPEIWEGE PPCLPPRDSL NQSLSQDLTM APGSTLWLSC

GVPPDSVSRG PLSWTHVHPK GPKSLLSLEL KDDRPARDMW

VMETGLLLPR ATAQDAGKYY CHRGNLTMSF HLEITARPVL

WHWLLRTGGW KVSAVTLAYL IFCLCSLVGI LHLQRALVLR

RKRKRMTDPT RRFFKVTPPP GSGPQNQYGN VLSLPTPTSG

LGRAQRWAAG LGGTAPSYGN PSSDVQADGA LGSRSPPGVG

PEEEEGEGYE EPDSEEDSEF YENDSNLGQD QLSQDGSGYE

NPEDEPLGPE DEDSFSNAES YENEDEELTQ PVARTMDFLS

PHGSAWDPSR EATSLAGSQS YEDMRGILYA APQLRSIRGQ

PGPNHEEDAD SYENMDNPDG PDPAWGGGGR MGTWSTR
```

In certain embodiments, the human CD19 comprises or consists of the amino acid sequence with a NCBI Reference No: NP_001761.3 (SEQ ID NO: 45), or a fragment thereof.

SEQ ID NO: 45 is provided below:

```
                                              [SEQ ID NO: 45]
MPPPRLLFFL LFLTPMEVRP EEPLVVKVEE GDNAVLQCLK

GTSDGPTQQL TWSRESPLKP FLKLSLGLPG LGIHMRPLAI

WLFIFNVSQQ MGGFYLCQPG PPSEKAWQPG WTVNVEGSGE

LFRWNVSDLG GLGCGLKNRS SEGPSSPSGK LMSPKLYVWA

KDRPEIWEGE PPCLPPRDSL NQSLSQDLTM APGSTLWLSC

GVPPDSVSRG PLSWTHVHPK GPKSLLSLEL KDDRPARDMW

VMETGLLLPR ATAQDAGKYY CHRGNLTMSF HLEITARPVL

WHWLLRTGGW KVSAVTLAYL IFCLCSLVGI LHLQRALVLR

RKRKRMTDPT RRFFKVTPPP GSGPQNQYGN VLSLPTPTSG

LGRAQRWAAG LGGTAPSYGN PSSDVQADGA LGSRSPPGVG

PEEEEGEGYE EPDSEEDSEF YENDSNLGQD QLSQDGSGYE

NPEDEPLGPE DEDSFSNAES YENEDEELTQ PVARTMDFLS

PHGSAWDPSR EATSLGSQSY EDMRGILYAA POLRSIRGQP

GPNHEEDADS YENMDNPDGP DPAWGGGGRM GTWSTR
```

In certain embodiments, the anti-CD19 antibodies and antigen binding fragments thereof described herein, bind to the extracellular domain of CD19. In certain embodiments, the anti-CD19 antibodies and antigen binding fragments thereof bind to the extracellular domain of human CD19. In certain embodiments, the extracellular domain of human CD19 comprises or consists of amino acids 20 to 291 of SEQ ID NO: 4. In certain embodiments, the extracellular domain of human CD19 comprises or consists of amino acids 20 to 291 of SEQ ID NO: 45.

In certain embodiments, the CD19 comprises or consists of an amino acid sequence that is at least about 80%, at least about 85%, at least about 90%, at least about 95%, at least about 96%, at least about 97%, at least about 98%, at least about 99%, or at least about 100% identical to the amino acid sequence set forth in SEQ ID NO: 4 or a fragment thereof.

In certain embodiments, the CD19 comprises or consists of an amino acid sequence that is at least about 80%, at least about 85%, at least about 90%, at least about 95%, at least about 96%, at least about 97%, at least about 98%, at least about 99%, or at least about 100% identical to the amino acid sequence set forth in SEQ ID NO: 45 or a fragment thereof.

An anti-CD19 antibody described herein can be an immunoglobulin, heavy chain antibody, light chain antibody, LRR-based antibody, or other protein scaffold with antibody-like properties, as well as other immunological binding moiety known in the art, including, e.g., a Fab, Fab', Fab'$_2$, Fab$_2$, Fab$_3$, F(ab')$_2$, Fd, Fv, Feb, scFv, SMIP, antibody, diabody, triabody, tetrabody, minibody, maxibody, tandab, DVD, BITER, TandAb, or the like, or any combination thereof. The subunit structures and three-dimensional configurations of different classes of antibodies are known in the art.

An antibody can be an immunoglobulin molecule of four polypeptide chains, e.g., two heavy (H) chains and two light (L) chains. A heavy chain can include a heavy chain variable domain and a heavy chain constant domain. A heavy chain constant domain can include CH1, hinge, CH2, CH3, and in some instances CH4 regions. A suitable heavy chain constant region may be derived from any immunoglobulin (e.g., IgA, IgG, or IgE). In some embodiments, a suitable heavy chain constant region may be derived from IgG1, IgG2, or IgG4. In particular embodiments, a suitable heavy chain constant region is derived from IgG1. A light chain can include a light chain variable domain and a light chain constant domain. A light chain constant domain can include either a kappa light chain or a lambda light chain. A heavy chain variable domain of a heavy chain and a light chain variable domain of a light chain can typically be further subdivided into regions of variability, termed complementarity determining regions (CDRs), interspersed with regions that are more conserved, termed framework regions (FR). Such heavy chain and light chain variable domains can each include three CDRs and four framework regions, arranged from amino-terminus to carboxyl-terminus in the following order: FR1, CDR1, FR2, CDR2, FR3, CDR3, FR4, one or more of which can be engineered as described herein. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987); Chothia et al. *Nature* 342:878-883 (1989). As used herein, CDRs are referred to for each of the heavy (HCDR1, HCDR2, HCDR3) and light (LCDR1, LCDR2, LCDR3) chains.

Embodiments of the invention include antibodies comprising the CDRs found in the vH and vL domains described herein that are identified using conventional numbering systems, such as the IMGT, Kabat and Clothia numbering systems. Such numbering systems are well-known in the art.

Heavy Chain Variable Region

In some embodiments, the anti-CD19 antibodies or fragments thereof described herein comprise a common heavy chain variable region. In some embodiments, the anti-CD19 antibody comprises heavy chain variable region (vH) complementarity determining region (CDR) sequences:

```
                                            (SEQ ID NO: 1)
    vH CDR1:       SYGMH (SEQ ID NO: 2)
    vH CDR2:       LIWYDGSNKYYADSVKG (SEQ ID NO: 3)
    vH CDR3:       PVEGLLRGFDY
```

In certain embodiments, the CDRs are identified according to the Kabat numbering system.

In some embodiments, the variable heavy chain comprises an amino acid sequence of

```
                                            (SEQ ID NO: 5)
QVQLVESGGGVVQPGRSLRLSCAASGFTFSSYGMHWVRQAPGKGLEWVAL

IWYDGSNKYYADSVKGRFTISRDNSKNTLYLQMNSLRAEDTAVYYCAKPV

EGLLRGFDYWGQGTLVTVSS.
```

In some embodiments, the anti-CD19 antibody comprises a heavy chain amino acid sequence having at least 85%, 90%, 91%, 92%, 93%, 94%, 95%, 96%, 97%, 98%, or 99% sequence identity to SEQ ID NO: 5.

In some embodiments, the anti-CD19 antibody comprises a heavy chain amino acid sequence having at least 85%, 90%, 91%, 92%, 93%, 94%, 95%, 96%, 97%, 98%, or 99% sequence identity to SEQ ID NO: 5 while also including one or more of the vH CDR1, vHCDR2, and/or vHCDR3 sequences described herein.

In some embodiments, the engineered antibodies comprise a heavy chain amino acid sequence identical to SEQ ID NO: 5. In certain embodiments, the $V_H$ comprises an amino acid sequence that is at least about 80% (e.g., at least about 85%, at least about 90%, or at least about 95%) identical or homologous to the amino acid sequence set forth in SEQ ID NO: 5. For example, the $V_H$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 5. In some embodiments, the anti-CD19 antibody comprises no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NO: 5.

In some embodiments, the anti-CD19 variable heavy chain is encoded by a polynucleotide that comprises the nucleic acid sequence of (SEQ ID NO: 6)
CAGGTGCAGCTGGTGGAGTCTGGGGGAGGCGTGGTCCAGCCTGGGAGGTC

CCTGAGACTCTCCTGTGCAGCGTCTGGATTCACCTTCAGTAGCTATGGCA

TGCACTGGGTCCGCCAGGCTCCAGGCAAGGGGCTGGAGTGGGTGGCACTG

ATATGGTATGATGGAAGTAATAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCGGTGTACTACTGCGCCAAGCCAGTG

GAAGGACTATTAAGAGGATTCGATTACTGGGGACAGGGTACATTGGTCAC

CGTCTCCTCA

In some embodiments, the anti-CD19 antibody comprises a heavy chain nucleic acid sequence having at least 85%, 90%, 95%, 98%, or 99% sequence identity to SEQ ID NO: 6. In some embodiments, the engineered antibodies comprise a heavy chain nucleic acid sequence identical to SEQ ID NO: 6. In some embodiments, the anti-CD19 antibody comprises a nucleic acid sequence that encodes an antibody comprising no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NO: 5.

In some embodiments, the anti-CD19 antibody is encoded by a polynucleotide that comprises a nucleic acid sequence encoding a heavy chain amino acid sequence having at least 85%, 90%, 95%, 98%, or 99% sequence identity to SEQ ID NO: 6, while also including one or more of the vH CDR1, vHCDR2, and/or vHCDR3 sequences described herein.

As will be understood by those of skill in the art, any such heavy chain CDR sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

In various engineered antibodies described herein, a heavy chain constant domain can be of any class (or subclass). In various engineered antibodies described herein, a heavy chain constant domain can include the amino acid sequence of any of one or more of IgG, IgM, IgA, IgD, or IgE, including subclasses such as IgG1, IgG2, IgG3, IgG4, IgA1, and IgA2. In various embodiments, a constant domain of engineered antibodies described herein can include a mixture of two or more classes (or subclasses) of immunoglobulin heavy chain constant domain. For example, an anti-CD19 antibody can include a first portion of a constant domain that has a sequence of an immunoglobulin constant domain selected from an IgG, IgM, IgA, IgD, or IgE class constant domain and a second portion of a constant domain that has a sequence of an immunoglobulin constant domain different from the first and selected from an IgG, IgM, IgA, IgD, or IgE class constant domain. In some instances, a constant domain of an anti-CD19 antibody described herein can include a mixture of two or more subclasses of a particular class of constant domain, e.g., a first portion of a constant domain that has a sequence of an immunoglobulin constant domain selected from an IgG1, IgG2, IgG3, or IgG4 subclass constant domain and a second portion of a constant domain that has a sequence of an immunoglobulin constant domain different from the first and selected from an IgG1, IgG2, IgG3, or IgG4 subclass constant domain. In some particular embodiments, a constant domain includes all or a portion of an IgG2 constant domain and all or a portion of an IgG4 constant domain.

In some instances, an anti-CD19 antibody includes an antibody constant region, Fc region or Fc fragment that exhibits altered binding (as compared to a reference constant region) to one or more Fc receptors (e.g., FcγRI, FcγRIIA, FcγRIIB, FcγRIIIA, FcγRIIIB, FcγRIV, or FcRn receptor). In some embodiments, a constant region, Fc region or Fc fragment is engineered to bind to a target (e.g., an FcRn receptor) in an altered manner (e.g., in a pH sensitive manner (e.g., in a more or less pH sensitive manner) and/or decreased or increased binding) relative to a reference constant region, Fc region or Fc fragment. In some embodiments, an anti-CD19 antibody includes an antibody constant region, Fc region or Fc fragment that exhibits decreased binding (as compared to a reference constant region) to one or more Fcγ receptor (e.g., FcγRI, FcγRIIA, FcγRIIB, FcγRIIIA, FcγRIIIB, or FcγRIV). In some embodiments, anti-CD19 antibody includes an antibody constant region, Fc region or Fc fragment that exhibits increased binding to the FcRn receptor (as compared to a reference constant region) at serum pH and/or at intracellular pH.

For example, an anti-CD19 antibody can include a constant region, Fc region or Fc fragment of an IgG antibody engineered to include an amino acid addition, deletion, or substitution, of one or more of amino acid residues 251-256, 285-290, 308-314, 385-389, and 428-436 (Kabat numbering (Kabat et al., (1991) Sequences of Proteins of Immunological Interest, NIH)). Without wishing to be bound by theory, it is believed that one or more of these constant region, Fc region, or Fc fragment amino acids mediate interaction with an Fc receptor, e.g., FcRn. In some embodiments, one or more of these disclosed amino acids is substituted with histidine, arginine, lysine, aspartic acid, glutamic acid, serine, threonine, asparagine, or glutamine. In some embodiments, a non-histidine residue is substituted with a histidine residue. In some embodiments, a histidine residue is substituted with a non-histidine residue.

In some embodiments, an anti-CD19 antibody includes a constant region, Fc region or Fc fragment of an IgG antibody having amino acid modifications at one or more of positions 308, 309, 311, 312, and 314, more specifically, having substitutions at one or more of positions 308, 309, 311, 312 and 314 with threonine, proline, serine, aspartic acid and leucine respectively. In some embodiments, residues at one or more of positions 308, 309, and 311 are substituted with isoleucine, proline, and glutamic acid, respectively. In yet other embodiments, residues at one or more of positions 308, 309, 311, 312, and 314, are substituted with threonine, proline, serine, aspartic acid, and leucine, respectively.

In some embodiments, an anti-CD19 antibody includes a constant region, Fc region or Fc fragment of an IgG antibody having amino acid modifications at one or more of positions 251, 252, 254, 255, and 256, more specifically, having substitutions at one or more of these positions. In some embodiments, residue 251 is substituted with leucine or arginine, residue 252 is substituted with leucine, tyrosine, phenylalanine, serine, tryptophan or threonine, residue 254 is substituted with threonine or serine, residue 255 is substituted with leucine, glycine, isoleucine or arginine, and/or residue 256 is substituted with serine, phenylalanine, arginine, glutamine, glutamic acid, aspartic acid, alanine, asparagine or threonine. In some embodiments, residue 251 is substituted with leucine, residue 252 is substituted with tyrosine or leucine, residue 254 is substituted with threonine or serine, and/or residue 255 is substituted with arginine. In yet other embodiments, residue 252 is substituted with phenylalanine and/or residue 256 is substituted with aspartic acid. In some embodiments, residue 251 is substituted with leucine, residue 252 is substituted with tyrosine, residue 254 is substituted with threonine or serine, and/or residue 255 is substituted with arginine.

In some embodiments, an anti-CD19 antibody includes a constant region, Fc region or Fc fragment of an IgG antibody having amino acid modifications at one or more of positions 428, 433, 434, 435, and 436, more specifically, having substitutions at one or more of these positions. In some embodiments, residue 428 is substituted with methionine, threonine, leucine, phenylalanine, or serine, residue 433 is substituted with lysine, arginine, serine, isoleucine, proline, glutamine, or histidine, residue 434 is substituted with phenylalanine, tyrosine, or histidine, residue 435 is substituted with tyrosine, and/or residue 436 is substituted with histidine, asparagine, arginine, threonine, lysine, methionine, or threonine. In some embodiments, residues at one or more positions 433, 434, 435, and 436 are substituted with lysine, phenylalanine, tyrosine, and histidine, respectively. In some embodiments, residue 428 is substituted with methionine and/or residue 434 is substituted with tyrosine.

In some embodiments, an anti-CD19 antibody includes a constant region, Fc region or Fc fragment of an IgG antibody having amino acid modifications at one or more of positions 385, 386, 387, and 389, more specifically, having substitutions at one or more of these positions. In some embodiments, residue 385 is substituted with arginine, aspartic acid, serine, threonine, histidine, lysine, or alanine, residue 386 is substituted with threonine, proline, aspartic acid, serine, lysine, arginine, isoleucine, or methionine, residue 387 is substituted with arginine, histidine, serine, threonine, alanine, or proline and/or residue 389 is substituted with proline or serine. In some embodiments, residues at one or more of positions 385, 386, 387, and 389 are substituted with arginine, threonine, arginine, and proline, respectively. In some embodiments, residues at one or more of positions 385, 386, and 389 are substituted with aspartic acid, proline, and serine, respectively.

In some embodiments, an anti-CD19 antibody includes a constant region, Fc region or Fc fragment of an IgG antibody having one or more of the following substitutions: leucine at residue 251, tyrosine or leucine at residue 252, threonine or serine at residue 254, arginine at residue 255, threonine at residue 308, proline at residue 309, serine at residue 311, aspartic acid at residue 312, leucine at residue 314, arginine at residue 385, threonine at residue 386, arginine at residue 387, proline at residue 389, methionine at residue 428, lysine at residue 433, phenylalanine or tyrosine at residue 434, tyrosine at position 435, and/or tyrosine at position 436. Additional amino acid substitutions that can be included in a constant region, Fc region or Fc fragment include those described in, e.g., U.S. Pat. Nos. 6,277,375; 8,012,476; and 8,163,881.

In some embodiments, an anti-CD19 antibody described herein includes a heavy chain constant domain that includes the Ala-Ala mutation described in, e.g., PCT Publication nos. WO 94/28027 and WO 98/47531; and Xu et al. (2000) Cell Immunol 200:16-26. Thus, in some embodiments, an anti-CD19 antibody with one or more mutations within the heavy chain constant region including the Ala-Ala mutation has reduced or no effector function. According to these embodiments, the constant region of an anti-CD19 antibody described herein can comprise a substitution to an alanine at position 234 and/or a mutation to an alanine at position 235 (EU numbering).

As will be understood by those of skill in the art, any such heavy chain constant domain sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

Light Chain Variable Region

The present invention additionally provides a CD19 antibody or fragment thereof comprising various specified sequences in one or more light chain variable regions, including in the light chain complementary determining regions LCDR1-3. In various embodiments, molecules with specified light chain variable regions are provided with heavy chain sequences as discussed above. In certain embodiments, the CDRs are identified according to the Kabat numbering system.

Thus, in one aspect, the present invention provides a CD19 antibody or fragment thereof comprising a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQAGAVPIT (SEQ ID NO: 12) (LCDR3).

In some embodiments, the CD19 antibody or fragment thereof comprises a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQVDSLHPFT (SEQ ID NO: 13) (LCDR3).

In some embodiments, the CD19 antibody or fragment thereof comprises a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPLT (SEQ ID NO: 14) (LCDR3).

In some embodiments, the CD19 antibody or fragment thereof comprises a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVRSSYLA (SEQ ID NO: 8) (LCDR1), GASSRAT (SEQ ID NO: 9) (LCDR2), and QQLFDSPYT (SEQ ID NO: 15) (LCDR3).

In some embodiments, the CD19 antibody or fragment thereof comprises a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVRSSYLA (SEQ ID NO: 8) (LCDR1), GASSRAT (SEQ ID NO: 9) (LCDR2), and QQAGVPPLT (SEQ ID NO: 16) (LCDR3).

In some embodiments, the CD19 antibody or fragment thereof comprises a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPFT (SEQ ID NO: 17) (LCDR3).

In some embodiments, the CD19 antibody or fragment thereof comprises a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASNRAT (SEQ ID NO: 10) (LCDR2), and QQAGVFPFT (SEQ ID NO: 18) (LCDR3).

In some embodiments, the CD19 antibody or fragment thereof comprises a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASRRAT (SEQ ID NO: 11) (LCDR2), and QQAGIPPYT (SEQ ID NO: 19) (LCDR3).

In some embodiments, the CD19 antibody or fragment thereof comprises an immunoglobulin light chain variable (VL) region comprising an amino acid sequence that is at least 90% identical to SEQ ID NO: 20; and an immunoglobulin heavy chain variable (VH) region comprising an amino acid sequence that is at least 90% identical to SEQ ID NO: 5.

In one aspect, the present invention provides a CD19 antibody or fragment thereof comprising an immunoglobulin light chain variable (VL) region comprising an amino acid sequence that is at least 90% identical to SEQ ID NOs: 20-27; and an immunoglobulin heavy chain variable (VH) region comprising an amino acid sequence that is at least 90% identical to SEQ ID NO: 5. In some embodiments, the VL region comprises an amino acid sequence that is at least 95% identical to SEQ ID NOs: 20-27.

In some embodiments, the anti-CD19 antibody or fragment thereof a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and/or comprises light chain variable region (vL) complementarity determining region (CDR) sequences shown in Table 1. In some embodiments, the anti-CD19 antibody or fragment thereof comprises light chain variable region (vL) complementarity determining region (CDR) sequences shown in Table 1:

TABLE 1

Anti-CD19 light chain variable CDRs

| Anti-CD19 Antibody | vL CDR1 | vL CDR2 | vL CDR3 |
|---|---|---|---|
| Antibody 2 | RASQSVSSSYLA (SEQ ID NO: 7) | GASSRAT (SEQ ID NO: 9) | QQAGAVPIT (SEQ ID NO: 12) |
| Antibody 4 | RASQSVSSSYLA (SEQ ID NO: 7) | GASSRAT (SEQ ID NO: 9) | QQVDSLHPFT (SEQ ID NO: 13) |
| Antibody 5 | RASQSVSSSYLA (SEQ ID NO: 7) | GASSRAT (SEQ ID NO: 9) | QQAGGVPPLT (SEQ ID NO: 14) |
| Antibody 8 | RASQSVRSSYLA (SEQ ID NO: 8) | GASSRAT (SEQ ID NO: 9) | QQLFDSPYT (SEQ ID NO: 15) |
| Antibody 6 | RASQSVRSSYLA (SEQ ID NO: 8) | GASSRAT (SEQ ID NO: 9) | QQAGVPPLT (SEQ ID NO: 16) |
| Antibody 7 | RASQSVSSSYLA (SEQ ID NO: 7) | GASSRAT (SEQ ID NO: 9) | QQAGGVPPFT (SEQ ID NO: 17) |
| Antibody 1 | RASQSVSSSYLA (SEQ ID NO: 7) | GASNRAT (SEQ ID NO: 10) | QQAGVFPFT (SEQ ID NO: 18) |
| Antibody 15 | RASQSVSSSYLA (SEQ ID NO: 7) | GASRRAT (SEQ ID NO: 11) | QQAGIPPYT (SEQ ID NO: 19) |

In some embodiments, the anti-CD19 antibody or fragment thereof comprises a light chain variable region (vL) with an amino acid sequences or encoded by a nucleic acid sequence shown in Table 2.

TABLE 2

Variable light chain sequences

| Anti-CD19 Antibody | vL Amino Acid Sequence | vL Nucleic Acid Sequence |
|---|---|---|
| Antibody 2 | EIVLTQSPGTLSLSPGERATLSCRASQSVSSS YLAWYQQKPGQAPRLLIYGASSRATGIPDRFS GSGSGTDFTLTISRLEPEDFAVYYCQQAGAVP ITFGGGTKVEIK (SEQ ID NO: 20) | GAAATTGTGTTGACGCAGTCTCCAGGCACCC TGTCTTTGTCTCCAGGGGAAAGAGCCACCCT CTCCTGCAGGGCCAGTCAGAGTGTTAGCAGC AGCTACTTAGCCTGGTACCAGCAGAAACCTG GCCAGGCTCCCAGGCTCCTCATCTATGGTGC ATCCAGCAGGGCCACTGGCATCCCAGACAGG TTCAGTGGCAGTGGGTCTGGGACAGACTTCA CTCTCACCATCAGCAGACTGGAGCCTGAAGA TTTTGCAGTGTATTACTGTCAGCAGGCCGGA GCCGTCCCTATCACTTTTGGCGGAGGGACCA AGGTTGAGATCAAA (SEQ ID NO: 28) |
| Antibody 4 | EIVLTQSPGTLSLSPGERATLSCRASQSVSSS YLAWYQQKPGQAPRLLIYGASSRATGIPDRFS GSGSGTDFTLTISRLEPEDFACYYCQQVDSLH PFTFGGGTKVEIK (SEQ ID NO: 21) | GAAATTGTGTTGACGCAGTCTCCAGGCACCC TGTCTTTGTCTCCAGGGGAAAGAGCCACCCT CTCCTGCAGGGCCAGTCAGAGTGTTAGCAGC AGCTACTTAGCCTGGTACCAGCAGAAACCTG GCCAGGCTCCCAGGCTCCTCATCTATGGTGC ATCCAGCAGGGCCACTGGCATCCCAGACAGG TTCAGTGGCAGTGGGTCTGGGACAGACTTCA CTCTCACCATCAGCAGACTGGAGCCTGAAGA TTTTGCAGTGTATTACTGTCAGCAGGTCGAC AGTCTCCATCCTTTCACTTTTGGCGGAGGGA CCAAGGTTGAGATCAAA (SEQ ID NO: 29) |
| Antibody 5 | EIVLTQSPGTLSLSPGERATLSCRASQSVSSS YLAWYQQKPGQAPRLLIYGASSRATGIPDRFS GSGSGTDFTLTISRLEPEDFAVYYCQQAGGVP PLTFGGGTKVEIK (SEQ ID NO: 22) | GAAATTGTGTTGACGCAGTCTCCAGGCACCC TGTCTTTGTCTCCAGGGGAAAGAGCCACCCT CTCCTGCAGGGCCAGTCAGAGTGTTAGCAGC AGCTACTTAGCCTGGTACCAGCAGAAACCTG GCCAGGCTCCCAGGCTCCTCATCTATGGTGC ATCCAGCAGGGCCACTGGCATCCCAGACAGG TTCAGTGGCAGTGGGTCTGGGACAGACTTCA CTCTCACCATCAGCAGACTGGAGCCTGAAGA TTTTGCAGTGTATTACTGTCAGCAGGCCGGA GGCGTCCCTCCTCTCACTTTTGGCGGAGGGA CCAAGGTTGAGATCAAA (SEQ ID NO: 30) |
| Antibody 8 | EIVLTQSPGTLSLSPGERATLSCRASQSVRSS YLAWYQQKPGQAPRLLIYGASSRATGIPDRFS GSGSGTDFTLTISRLEPEDFAVYYCQQLFDSP YTFGGGTKVEIK (SEQ ID NO: 23) | GAAATTGTGTTGACGCAGTCTCCAGGCACCC TGTCTTTGTCTCCAGGGGAAAGAGCCACCCT CTCCTGCAGGGCCAGTCAGAGTGTTAGGAGC AGCTACTTAGCCTGGTACCAGCAGAAACCTG GCCAGGCTCCCAGGCTCCTCATCTATGGTGC ATCCAGCAGGGCCACTGGCATCCCAGACAGG TTCAGTGGCAGTGGGTCTGGGACAGACTTCA CTCTCACCATCAGCAGACTGGAGCCTGAAGA TTTTGCAGTGTATTACTGTCAGCAGCTCTTC GACAGTCCTTACACTTTTGGCGGAGGGACCA AGGTTGAGATCAAA (SEQ ID NO: 31) |
| Antibody 6 | EIVLTQSPGTLSLSPGERATLSCRASQSVRSS YLAWYQQKPGQAPRLLIYGASSRATGIPDRFS GSGSGTDFTLTISRLEPEDFAVYYCQQAGVPP LTFGGGTKVEIK (SEQ ID NO: 24) | GAAATTGTGTTGACGCAGTCTCCAGGCACCC TGTCTTTGTCTCCAGGGGAAAGAGCCACCCT CTCCTGCAGGGCCAGTCAGAGTGTTAGGAGC AGCTACTTAGCCTGGTACCAGCAGAAACCTG GCCAGGCTCCCAGGCTCCTCATCTATGGTGC ATCCAGCAGGGCCACTGGCATCCCAGACAGG TTCAGTGGCAGTGGGTCTGGGACAGACTTCA CTCTCACCATCAGCAGACTGGAGCCTGAAGA TTTTGCAGTGTATTACTGTCAGCAGGCCGGA GTCCCCCCTCTCACTTTTGGCGGAGGGACCA AGGTTGAGATCAAA (SEQ ID NO: 32) |
| Antibody 7 | EIVMTQSPGTLSLSPGERATLSCRASQSVSSS YLAWYQQKPGQAPRLLIYGASSRATGIPDRFS GSGSGTDFTLTISRLEPEDFAVYYCQQAGGVP PFTFGGGTKVEIK (SEQ ID NO: 25) | GAAATTGTGATGACGCAGTCTCCAGGCACCC TGTCTTTGTCTCCAGGGGAAAGAGCCACCCT CTCCTGCAGGGCCAGTCAGAGTGTTAGCAGC AGCTACTTAGCCTGGTACCAGCAGAAACCTG GCCAGGCTCCCAGGCTCCTCATCTATGGTGC ATCCAGCAGGGCCACTGGCATCCCAGACAGG TTCAGTGGCAGTGGGTCTGGGACAGACTTCA CTCTCACCATCAGCAGACTGGAGCCTGAAGA TTTTGCAGTGTATTACTGTCAGCAGGCCGGA GGCGTCCCTCCTTTCACTTTTGGCGGAGGGA |

TABLE 2-continued

Variable light chain sequences

| Anti-CD19 Antibody | vL Amino Acid Sequence | vL Nucleic Acid Sequence |
|---|---|---|
| | | CCAAGGTTGAGATCAAA<br>(SEQ ID NO: 33) |
| Antibody 1 | EIVMTQSPGTLSLSPGERATLSCRASQSVSSS<br>YLSWYQQKPGQAPRLLIYGASNRATGIPDRFS<br>GSGSGTDFTLTISRLEPEDFAVYYCQQAGVFP<br>FTFGGGTKVEIK<br>(SEQ ID NO: 26) | GAAATTGTGATGACGCAGTCTCCAGGCACCC<br>TGTCTTTGTCTCCAGGGGAAAGAGCCACCCT<br>CTCCTGCAGGGCCAGTCAGAGTGTTAGCAGC<br>AGCTACTTAGCCTGGTACCAGCAGAAACCTG<br>GCCAGGCTCCCAGGCTCCTCATCTATGGTGC<br>ATCCAACAGGGCCACTGGCATCCCAGACAGG<br>TTCAGTGGCAGTGGGTCTGGGACAGACTTCA<br>CTCTCACCATCAGCAGACTGGAGCCTGAAGA<br>TTTTGCAGTGTATTACTGTCAGCAGGCCGGA<br>GTCTTCCCTTTCACTTTTGGCGGAGGGACCA<br>AGGTTGAGATCAAA<br>(SEQ ID NO: 34) |
| Antibody 15 | EIVLTQSPGTLSLSPGERATLSCRASQSVSSS<br>YLAWYQQKPGQAPRLLIYGASSRATGIDPRFS<br>GSGSGTDFTLTISRLEPEDFAVYYCQQAGIPP<br>YTFGGGTKVEIK<br>(SEQ ID NO: 27) | GAAATTGTGTTGACGCAGTCTCCAGGCACCC<br>TGTCTTTGTCTCCAGGGGAAGAGCCACCCTC<br>TCCTGCAGGGCCAGTCAGAGTGTTAGCAGCA<br>GCTACTTAGCCTGGTACCAGCAGAAACCTGG<br>CCAGGCTCCCAGGCTCCTCATCTATGGTGCA<br>TCCAGAAGGGCCACTGGCATCCCAGACAGGT<br>TCAGTGGCAGTGGGTCTGGGACAGACTTCAC<br>TCTCACCATCAGCAGACTGGAGCCTGAAGAT<br>TTTGCAGTGTATTACTGTCAGCAGGCCGGCA<br>TCCCCCCTTACACTTTTGGCGGAGGGACCAA<br>GGTTGAGATCAAA<br>(SEQ ID NO: 35) |

In some embodiments, the anti-CD19 antibody comprises a light chain amino acid sequence having at least 85%, 90%, 91%, 92%, 93%, 94%, 95%, 96%, 97%, 98%, or 99% sequence identity to SEQ ID NOs: 20-27.

In some embodiments, the anti-CD19 antibody comprises a light chain amino acid sequence having at least 85%, 90%, 95%, 98%, or 99% sequence identity to SEQ ID NOs: 20-27 while also including one or more of the vL CDR1, vLCDR2, and/or vLCDR3 sequences described herein.

In some embodiments, the anti-CD19 antibody or fragment thereof comprises a light chain amino acid sequence identical to SEQ ID NOs: 20-27. In some embodiments, the anti-CD19 antibody comprises no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NOs: 20-27.

In some embodiments, a nucleic acid sequence of the invention encodes an anti-CD19 antibody comprising a light chain amino acid sequence having at least 85%, 90%, 95%, 98%, or 99% sequence identity to SEQ ID NOs: 20-27 while also including one or more of the vL CDR1, vLCDR2, and/or vLCDR3 sequences described herein.

As will be understood by those of skill in the art, any such light chain CDR sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

In some embodiments, an anti-CD19 antibody described herein includes a light chain that includes any light chain constant domain sequence, e.g., a constant sequence of a light chain known to those of skill in the art. As those of skill in the art will be aware, a light chain constant domain may be a kappa light chain constant domain or a lambda light chain constant domain. In certain embodiments, the constant domain of a light chain as disclosed herein is a kappa light chain constant domain. In various embodiments, an anti-CD19 antibody described herein includes a light chain constant domain.

Exemplary Antibodies

Engineered antibodies can include various heavy chains and light chains described herein. In some embodiments, an anti-CD19 antibody can include two heavy chains and light chains. In various embodiments, the present disclosure encompasses an antibody including at least one heavy chain and/or light chain as disclosed herein, at least one heavy chain and/or light chain framework domain as disclosed herein, at least one heavy chain and/or light chain CDR domain as disclosed herein, and/or any heavy chain and/or light chain constant domain as disclosed herein.

In various embodiments, an anti-CD19 antibody disclosed herein is a homodimeric monoclonal antibody. In various embodiments, an anti-CD19 antibody disclosed herein is a heterodimeric antibody. In various embodiments, an anti-CD19 antibody is, e.g., a typical antibody or a diabody, triabody, tetrabody, minibody, maxibody, tandab, DVD, BiTE®, scFv, TandAb scFv, Fab, Fab$_2$, Fab$_3$, F(ab')$_2$, or the like, or any combination thereof.

In some embodiments, the disclosure provides fusion proteins comprising one or more variable domains or engineered antibodies as described herein, or portion thereof, and one or more additional polypeptides.

Exemplary Single Chain Variable Fragments

In some embodiments, the disclosure provides a single-chain variable fragment. In some embodiments, the scFv is a human scFv. A "single-chain variable fragment" or "scFv" refers to a fusion protein of the variable regions of the heavy (VH) and light chains (VL) of an immunoglobulin (e.g., mouse or human) covalently linked to form a VH:: VL heterodimer. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6): 1910$^{-1917}$ (2008) and WO 2014/087010, the contents of which are hereby incorporated by reference in their entireties. In certain embodiments, the linker is a G4S linker (SEQ ID NO: 46).

Alternatively or additionally, the scFv may be derived from Fab's (instead of from an antibody, e.g., obtained from Fab libraries). In certain embodiments, the anti-CD19 antibody or fragment thereof is a Fab. In certain embodiments, the Fab is crosslinked. In certain embodiments, the anti-CD19 antibody or fragment thereof is a F(ab)$_2$. Any of the foregoing molecules may be comprised in a fusion protein with a heterologous sequence to form an anti-CD19 antigen antibody or an antigen-binding fragment thereof.

In certain embodiments, the anti-CD19 antibody or fragment thereof binds to CD19 (e.g., human CD19) with a dissociation constant (Kd) of at least about $1\times10^6$ M, at least about $1\times10^{-7}$ M, at least about $1\times10^{-8}$ M, at least about $1\times10^{-9}$ M, or at least about $1\times10^{-10}$ M. In certain embodiments, the anti-CD19 antibody or fragment thereof binds to CD19 (e.g., human CD19) with a dissociation constant (Kd) of at least about $2\times10^{-8}$ M. In certain embodiments, the anti-CD19 antibody or fragment thereof binds to CD19 (e.g., human CD19) with a dissociation constant (Kd) of between about $2\times10^{-8}$ M and about $8\times10^{-9}$ M.

In some embodiments, the anti-CD19 antibody or fragment thereof binds to CD19 (e.g., human CD19) with a dissociation constant (Kd) between about 1 nM and 50 nM, about 5 nM and 30 nM, about 5 nM and 25 nM, or about 8 nM and 20 nM. In some embodiments, the anti-CD19 antibody or fragment thereof binds to CD19 (e.g., human CD19) with a dissociation constant (Kd) of at least about 50 nM, at least about 40 nM, at least about 35 nM, at least about 30 nM, at least about 25 nM, at least about 20 nM, at least about 19 nM, at least about 18 nM, at least about 17 nM, at least about 16 nM, at least about 15 nM, at least about 14 nM, at least about 13 nM, at least about 12 nM, at least about 11 nM, at least about 10 nM, at least about 9 nM, at least about 8 nM, at least about 7 nM, at least about 6 nM, at least about 5 nM.

In some embodiments, the anti-CD19 scFv comprises a variable heavy chain comprising SEQ ID Nos: 1-4. In some embodiments, the anti-CD19 scFv comprises a variable light chain comprising one or more CDR sequences provided in Table 1. In some embodiments, the anti-CD19 scFv comprises a variable light chain comprising one or more light chain sequences provided in Table 2.

In some embodiments, the anti-CD19 scFv comprises a linker comprises or consists of the amino acid sequence set forth in SEQ ID NO: 36, which is provided below:

[SEQ ID NO: 36]
GGGGSGGGGSGGGGS

In some embodiments, the linker comprises or consists of the amino acid sequence set forth in SEQ ID NO: 37, which is provided below:

[SEQ ID NO: 37]
GGGGSGGGGSGGGSGGGGS

In some embodiments, the linker comprises or consists of the amino acid sequence set forth in SEQ ID NO: 38, which is provided below:

[SEQ ID NO: 38]
GGGGSGGGGSGGGGSGGGSGGGGS

In some embodiments, the linker comprises or consists of the amino acid sequence set forth in SEQ ID NO: 39, which is provided below:

[SEQ ID NO: 39]
GGGGSGGGGSGGGGSGGGGSGGGSGGGGS

In some embodiments, the anti-CD19 antibody or fragment thereof comprises a conservative sequence modification (e.g., anti-CD19 antibody or fragment thereof described herein). In some embodiments, the conservative sequence modification is an amino acid modification that does not significantly affect or alter the binding characteristics of the presently disclosed anti-CD19 antibody or fragment thereof (e.g., the antibody or fragment thereof) comprising the amino acid sequence. Conservative modifications can include amino acid substitutions, additions and deletions. Modifications can be introduced into the anti-CD19 antibodies or fragments thereof by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function. In certain embodiments, no more than one, no more than two, no more than three, no more than four, no more than five residues within a specified sequence or a CDR region are altered.

In some embodiments, the light chain and/or heavy chain of the anti-CD19 scFv comprise a signal peptide. In some embodiments, the signal peptide comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% homology or identity to the amino acid sequence

```
                                                  (SEQ ID NO: 40)
              MDMRVPAQLLGLLLLWLPDTRC,
              or (SEQ ID NO: 41)
              MEFGLSWVFLVALLRGVQC.
```

In some embodiments, the anti-CD19 scFv comprises an amino acid sequence set forth in SEQ ID NO: 42.

```
                                                  [SEQ ID NO: 42]
EIVLTQSPGTLSLSPGERATLSCRASQSVSSSYLAWYQQKPGQAPRLLIY

GASSRATGIPDRFSGSGSGTDFTLTISRLEPEDFAVYYCQQAGAVPITFG

GGTKVEIKGGGGSGGGGSGGGGSQVQLVESGGGVVQPGRSLRLSCAASGF

TFSSYGMHWVRQAPGKGLEWVALIWYDGSNKYYADSVKGRFTISRDNSKN

TLYLQMNSLRAEDTAVYYCAKPVEGLLRGFDYWGQGTLVTVSS
```

In some embodiments, anti-CD19 scFv comprises an amino acid sequence sequence having at least 70%, at least 75%, at least 80%, at least 85%, at least 90%, at least 91%, at least 92%, at least 93%, at least 94%, at least 95%, at least 96%, at least 97%, at least 98%, or at least 99% homology or identity to SEQ ID NO: 42.

In some embodiments, the anti-CD19 scFv comprises an amino acid sequence set forth in SEQ ID NO: 43.

```
                                                  [SEQ ID NO: 43]
EIVLTQSPGTLSLSPGERATLSCRASQSVRSSYLAWYQQKPGQAPRLLIY

GASSRATGIPDRFSGSGSGTDFTLTISRLEPEDFAVYYCQQLFDSPYTFG

GGTKVEIKGGGGSGGGGSGGGGSQVQLVESGGGVVQPGRSLRLSCAASGF

TFSSYGMHWVRQAPGKGLEWVALIWYDGSNKYYADSVKGRFTISRDNSKN

TLYLQMNSLRAEDTAVYYCAKPVEGLLRGFDYWGQGTLVTVSS
```

In some embodiments, anti-CD19 scFv comprises an amino acid sequence sequence having at least 70%, at least 75%, at least 80%, at least 85%, at least 90%, at least 91%, at least 92%, at least 93%, at least 94%, at least 95%, at least 96%, at least 97%, at least 98%, or at least 99% homology or identity to SEQ ID NO: 43.

In some embodiments, the anti-CD19 scFv comprises an amino acid sequence set forth in SEQ ID NO: 44.

```
                                                  [SEQ ID NO: 44]
QVQLVESGGGVVQPGRSLRLSCAASGFTFSSYGMHWVRQAPGKGLEWVAL

IWYDGSNKYYADSVKGRFTISRDNSKNTLYLQMNSLRAEDTAVYYCAKPV

EGLLRGFDYWGQGTLVTVSSGGGGSGGGGSGGGGSEIVLTQSPGTLSLSP

GERATLSCRASQSVSSSYLAWYQQKPGQAPRLLIYGASRRATGIPDRFSG

SGSGTDFTLTISRLEPEDFAVYYCQQAGIPPYTFGGGTKVEIK
```

In some embodiments, anti-CD19 scFv comprises an amino acid sequence sequence having at least 70%, at least 75%, at least 80%, at least 85%, at least 90%, at least 91%, at least 92%, at least 93%, at least 94%, at least 95%, at least 96%, at least 97%, at least 98%, or at least 99% homology or identity to SEQ ID NO: 44.

Nucleotide Sequences

The present disclosure includes nucleotide sequences encoding one or more heavy chains, heavy chain variable domains, heavy chain framework regions, heavy chain CDRs, heavy chain constant domains, light chains, light chain variable domains, light chain framework regions, light chain CDRs, light chain constant domains, or other immunoglobulin-like sequences, or antibodies disclosed herein. In various embodiments, such nucleotide sequences may be present in a vector. In various embodiments such nucleotides may be present in the genome of a cell, e.g., a cell of a subject in need of treatment or a cell for production of an antibody, e.g. a mammalian cell for production of a an antibody.

Engineered Antibodies and Fusion Proteins

In some embodiments, the disclosure provides fusion proteins comprising (i) one or more antigen-binding regions described herein (e.g., antigen-binding region of immunoglobulin, heavy chain antibody, light chain antibody, LRR-based antibody, or other protein scaffold with antibody-like properties, as well as other antigen binding moiety known in the art, including, e.g., a Fab, Fab', Fab'$_2$, Fab$_2$, Fab$_3$, F(ab')$_2$, Fd, Fv, Feb, scFv, SMIP, antibody, diabody, triabody, tetrabody, minibody, maxibody, tandab, DVD, BiTE®, TandAb, or the like), e.g., one or more variable domains described herein, or portion thereof (e.g., one or more CDRs described herein), and (ii) one or more additional polypeptides. For example, albumin is an abundant serum protein that is protected from degradation by pH-dependent recycling mediated by interaction with FcRn. In some embodiments, one or more variable domains or engineered antibodies as described herein, or portion thereof (e.g., one or more CDRs described herein) is fused to albumin, a portion thereof (such as a portion of albumin that binds to an FcRn), and/or an engineered variant of albumin that binds to FcRn with improved affinity. In other instances, one or more variable domains or engineered antibodies as described herein, or portion thereof (e.g., one or more CDRs described herein) is fused to a polypeptide that binds to albumin to form a fusion protein-albumin complex, which can in turn bind to an FcRn. In some embodiments, the polypeptide that binds to albumin is a single chain variable fragment (scFv). The albumin or portion thereof can include a mutation of one or more amino acids that can modify its binding to an FcRn. Such mutations are known in the art (see, e.g., Andersen et al., *Nature Communications* 3:610 doi: 10.1038/nocmms1607 (2012)). In other instances, one or more variable domains or engineered antibodies described herein, or portion thereof (e.g., one or more CDRs described herein) is fused to transferrin. Transferrin is recycled by binding to a transferrin receptor (see, e.g., Widera et al., *Adv. Drug Deliv. Rev.* 55:1439-66 (2003)).

pH-Dependent Binding of Anti-CD19 Antibody with CD19 and/or Fc Receptor

Engineered antibodies described herein can be engineered to exhibit pH-dependency, or enhanced pH dependency, in affinity for CD19 (e.g., mediated by one or more variable domains described herein), and/or altered (e.g., increased, e.g., pH dependent) affinity for FcRn (e.g., mediated by one or more constant domains described herein). For example, in some embodiments an antibody capable of binding CD19, or a variable domain capable of binding CD19, binds CD19 with higher affinity at a serum pH (e.g., at a neutral pH or at a pH above 7.4) than at a compartmental (e.g., endosomal) pH (e.g., at an acidic pH or at a pH equal to or less than pH 6.0). In various embodiments in which CD19 is bound by an antibody having pH-dependent CD19 binding, a transition of pH from serum pH to compartmental pH (e.g., from serum to endosome) facilitates separation of CD19 and antibody (i.e., "unbinding") at compartmental pH and/or in a particular compartment, e.g., endosome. In various embodiments, such pH-dependent binding can mediate antibody recycling and/or CD19 degradation. In particular instances, a transition from serum pH to compartmental pH (e.g., from serum to endosome) facilitates separation of CD19 and antibody (i.e., "unbinding") at the compartmental pH and/or in a particular compartment, e.g., endosome, such that the antibody is recycled out by FcRn and the antigen is degraded in a lysosome. In some such instances, the pH-dependency of CD19 binding improves the "processivity" of the antibody at least in that, upon recycling, the antibody is returned to serum and is free to bind target circulating CD19. In some instances, recycling of an antibody that displays pH-dependent CD19 binding can continue until the antibody eventually degrades or is degraded, by which time a single antibody molecule may have bound and mediated the inactivation of a plurality of CD19 molecules, rather than just one.

In certain embodiments, an anti-CD19 antibody disclosed herein includes a constant domain (e.g., an Fc domain) displaying increased affinity relative to control for an Fc receptor, such as FcRn. In some embodiments, such increased affinity relative to control is at a pH value for serum (e.g., pH greater than 6.8, 6.9, 7.0, 7.1, 7.2, 7.3, 7.4, 7.5, 7.6, 7.7, 7.8, 7.9, 8.0, 8.1, 8.2, or greater). In some embodiments, such increased affinity relative to control is at a compartmental pH (e.g., a pH lower than 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or lower). In certain embodiments, an anti-CD19 antibody disclosed herein includes a constant domain (e.g., an Fc domain) displaying pH-dependency (or enhanced pH dependency relative to control in affinity for an Fc receptor, such as FcRn. The neonatal Fc receptor (FcRn) is a MHC class I like molecule that functions to protect IgG and albumin from catabolismmediates transport of IgG across epithelial cells, and is involved in antigen presentation by professional antigen presenting cells. IgG antibody subtypes exhibit long serum half-lives, primarily due to the scavenging of antibodies from the endosomes by FcRn that recycles IgGs back out of cells.

In some embodiments, serum half-life of an anti-CD19 antibody is increased. For example, binding of an anti-CD19 antibody to FcRn increases serum half-life of the antibody to about 4 days to about 45 days, e.g., about 5 days to about 30 days, about 10 days to about 30 days, or about 20 days to about 30 days. In certain embodiments, an anti-CD19 antibody described herein has a serum half-life of about 5 days, about 10 days, about 15 days, about 20 days, about 25 days, about 30 days, about 35 days, about 40 days, about 45 days, about 50 days or longer.

In certain embodiments, an anti-CD19 antibody described herein exhibits a pH-dependent change in affinity for CD19. Affinity may be measured as a $K_D$, equilibrium dissociation constant, of antibody and antigen; $K_D$ and affinity are inversely related. In various embodiments, $K_D$ of an anti-CD19 antibody as described herein for CD19 at a serum pH (e.g., a pH greater than 6.8, 6.9, 7.0, 7.1, 7.2, 7.3, 7.4, 7.5, 7.6, 7.7, 7.8, 7.9, 8.0, 8.1, 8.2, or greater) or under serum conditions is less than about $10^{-4}$, $10^{-5}$, $10^{-6}$, $10^{-7}$, $10^{-8}$, $10^{-9}$, $10^{-10}$, $10^{-11}$, $10^{12}$, $10^{-13}$ $10^{-14}$, or $10^{-15}$ M. In certain instances, $K_D$ of an antibody as described herein for CD19 at a serum pH is between 0.001 and 1 nM, e.g., 0.001 nM, 0.005 nM, 0.01 nM, 0.05 nM, 0.1 nM, 0.5 nM, or 1 nM. In some embodiments, $K_D$ for CD19 at a compartmental pH (e.g., a pH lower than 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or lower) or under compartmental conditions is higher than $K_D$ of the same antibody for CD19 at a serum pH or under serum conditions (and/or affinity of antibody for CD19 at compartmental pH or under compartmental conditions may be decreased relative to affinity at a serum pH or under serum conditions) by, e.g., at least 2-fold, e.g., 2-fold, 3-fold, 4-fold, 5-fold, 6-fold, 7-fold, 8-fold, 9-fold, 10-fold, 20-fold, 30-fold, 40-fold, 50-fold, 75-fold, 100-fold 150-fold, 200-fold, 250-fold, 300-fold, 350-fold, 400-fold, 450-fold, 500-fold, 600-fold, 700-fold, 800-fold, 900-fold, 1000-fold, 2,000-fold, 3,000-fold, 4,000-fold, 5,000-fold, 6,000-fold, 7-000 fold, 8,000-fold, 9,000-fold, 10,000-fold, or more. In some embodiments, $K_D$ for CD19 at a compartmental pH (e.g., a pH lower than 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or lower) or under compartmental conditions may be, e.g., greater than $10^{-15}$, $10^{-14}$, $10^{-13}$, $10^{-12}$, $10^{-11}$, $10^{-10}$, $10^{-9}$, $10^{-8}$, $10^{-7}$, $10^{-6}$, $10^{-5}$, $10^{-4}$, or $10^{-3}$ M. In certain instances, $K_D$ of an anti-CD19 antibody as described herein for CD19 at a compartmental pH or under compartmental conditions may be, e.g., equal to or greater than 1 nM, e.g., 1 nM, 2 nM, 3 nM, 4 nM, 5 nM, 10 nM, 20 nM, 30 nM, 40 nM, 50 nM, 100 nM, 200 nM, 300 nM, 400 nM, 500 nM, 600 nM, 700 nM, 800 nM, 900 nM, 1 mM, or more.

In some embodiments, an anti-CD19 antibody described herein exhibits a greater half-life than a reference antibody (e.g., an antibody that cross-competes for CD19 binding) when administered to a subject, e.g., in the serum of the subject. In various embodiments, the half-life of a reference antibody (e.g., an antibody that cross-competes for CD19 binding) in serum may be, e.g., 250 to 300 hours. In various embodiments, the half-life in serum of an anti-CD19 antibody as described herein may be, e.g., at least 250 hours, e.g., at least 260, 270, 280, 290, or 300 hours. In certain embodiments, the half-life in serum of an anti-CD19 antibody as described herein may be at least 300 hours, e.g., at least 350, 400, 450, 500, 550, 600, 650, 700, 750, 800, 850, 900, 950, or 1,000 hours. In certain embodiments, the half-life in serum of an anti-CD19 antibody as described herein may be at least 1,000 hours, e.g., at least 1,500, 2,000, 2,500, 3,000, 3,500, 4,000, 4,500, 5,000, 6,000, 7,000, 8,000, 9,000, 10,000, 11,000, 12,000, 13,000, 14,000, or 15,000 hours or more. In various embodiments, the half-life in serum of an anti-CD19 antibody as described herein may be at least 12 days, 15 days, 20 days, 25 days, 30 days, 35 days, 40 days, 45 days, 50 days, 2 months, 3 months, 4 months, 5 months, 6 months, or more. In various embodiments, the half-life in serum of an anti-CD19 antibody as described herein may be increased as compared to a reference antibody (e.g., an antibody that cross-competes for CD19 binding) by a factor of at least, e.g., 2-fold, 3-fold, 4-fold, 5-fold, 6-fold, 7-fold, 8-fold, 9-fold, 10-fold, 20-fold, 30-fold, 40-fold, 50-fold, 75-fold, 100-fold or more.

In certain embodiments, an anti-CD19 antibody described herein exhibits an increased half-life in plasma, an increased mean retention time in plasma, and/or an increased level of CD19 clearance (e.g., an antibody that cross-competes for CD19 binding). These parameters can be determined by methods known to those skilled in the art (e.g., as described in Nestorov et al., J. Clin. Pharmacol. 48:406-417 (2008); Leveque et al., Anticancer Research 25:2327-2344 (2005); Igawa et al., PLOS One 8: e63236. Doi: 10.1371/journal-.pone.0063236 (2013)). For example, an anti-CD19 antibody described herein (e.g., a single dose of such anti-CD19 antibody) reduces the level of CD19 in plasma by at least 10-fold, 50-fold, 100-fold, 250-fold, 500-fold, 750-fold, 1000-fold, 1500-fold, or more, relative to a reference antibody.

Engineered Antibodies and Fragments Thereof

CD19 antibodies and fragments thereof according to the present disclosure are engineered to include one or more binding moieties that specifically bind one or more targets of interest in a pH-dependent manner. CD19 antibodies and fragments thereof encompass nucleic acids (e.g., RNA and DNA), proteins (e.g., antibodies), and combination thereof. pH-dependent binding moieties can be or include, for example, nucleic acids (e.g., RNA and DNA) and aptamers, polypeptides (e.g., antibodies or fragments thereof, albumin, receptors, ligands, signal peptides, avidin, and Protein A), polysaccharides, biotin, hydrophobic groups, hydrophilic groups, drugs, and any organic molecules that bind to receptors.

Antibody or Fragment Thereof as Binding Moieties

In some embodiments, an antibody or fragment thereof described herein is an anti-CD19 antibody. In some instances, one or more binding moieties described herein are or include antibodies, antigen-binding fragments thereof, and/or Fc regions (or Fc fragments) thereof. The basic structure of an IgG antibody consists of two identical light polypeptide chains and two identical heavy polypeptide chains linked together by disulphide bonds. The first domain located at the amino terminus of each chain is variable in amino acid sequence, providing antibody binding specificities found in each individual antibody. These are known as variable heavy (VH) and variable light (VL) regions. The other domains of each chain are relatively invariant in amino acid sequence and are known as constant heavy (CH) and constant light (CL) regions. For an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')₂ fragments, disulfide-linked Fvs (sdFv), anti-idiotypic (anti-Id) antibodies (including, e.g., anti-anti-Id antibodies), minibodies, domain antibodies, synthetic antibodies (sometimes referred to as "antibody mimetics"), and antigen-binding fragments of any of the above. In certain embodiments, antibodies described herein refer to polyclonal antibody populations.

The term "Fc fragment", as used herein, refers to one or more fragments of an Fc region that retains an Fc function and/or activity described herein, such as binding to an Fc receptor. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')₂ fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and fragments can be screened for utility in the same manner as are intact antibodies.

In some aspects the present invention provides antibodies or fragments thereof that bind to human CD19comprising human heavy and/or light constant regions, wherein the human heavy constant region comprises an isotypic variant comprising the Fc region of human IgG1, human IgG2, human IgG3, or human IgG4.

In a further aspect the present invention provides a humanized antibody or fragment thereof that binds to human CD19, wherein the antibody comprises a variant human IgG Fc region which comprises amino acid substitution S324N replacing serine at amino acid position 324 of the parent antibody with asparagine, whereas the antibody comprising the variant human IgG Fc region exhibits improved complement dependent cytotoxicity (CDC) compared to the parent antibody.

Antibodies or fragments can be produced by any method known in the art for synthesizing antibodies (see, e.g., Harlow et al., Antibodies: A Laboratory Manual, (Cold Spring Harbor Laboratory Press, 2$^{nd}$ ed. 1988); Brinkman et al., 1995, J. Immunol. Methods 182:41-50; WO 92/22324; WO 98/46645). Chimeric antibodies can be produced using methods described in, e.g., Morrison, 1985, Science 229: 1202, and humanized antibodies by methods described in, e.g., U.S. Pat. No. 6,180,370.

Additional compositions and methods described herein are bispecific antibodies and multivalent antibodies, as described in, e.g., Segal et al., J. Immunol. Methods 248:1-6 (2001); and Tutt et al., J. Immunol. 147: 60 (1991).

Engineered Antigen Binding Regions

In some embodiments, a binding moiety is or includes an antibody (e.g., an IgG antibody, e.g., an IgG1, IgG2, or IgG3 antibody), or an antigen binding fragment, engineered to bind to a target (i.e., antigen) in an altered manner (e.g., in a pH sensitive manner, e.g., in a more or less pH sensitive manner) relative to a reference antibody or antigen binding fragment. For example, an antibody can be engineered by modifying (e.g., by adding, deleting, or substituting) an amino acid within one or more antibody CDRs and/or at a position involved in antibody CDR structure. Exemplary, non-limiting sites of an antibody that can be modified include the following (amino acid positions are indicated based on the Kabat numbering (Kabat et al., (1991) Sequences of Proteins of Immunological Interest, NIH)).

Heavy chain: H27, H31, H32, H33, H35, H50, H58, H59, H61, H62, H63, H64, H65, H99, H100b, and H102

Light chain: L24, L27, L28, L32, L53, L54, L56, L90, L92, and L94.

In some embodiments, one or more of these disclosed amino acids can be substituted with histidine, arginine, lysine, aspartic acid, glutamic acid, serine, threonine, asparagine, or glutamine. Without wishing to be bound by theory, it is believed that substituting an amino acid at one or more of these positions with a histidine can result in an antibody having pH-dependent antigen-binding properties. In some embodiments, a non-histidine residue is substituted with a histidine residue. In some embodiments, a histidine residue is substituted with a non-histidine residue. Additional engineered antigen binding regions include those described in, e.g., U.S. Publ. No. 20110229489.

Engineered Constant Regions

In some instances, a binding moiety is or includes an antibody constant region, Fc region or Fc fragment that binds one or more Fc receptors (e.g., FcγRI, FcγRIIA, FcγRIIB, FcγRIIIA, FcγRIIIB, FcγRIV, or FcRn receptor). In some embodiments, a constant region, Fc region or Fc fragment is engineered to bind to a target (e.g., an Fc receptor) in an altered manner (e.g., in a pH sensitive manner, e.g., in a more or less pH sensitive manner) relative to a reference constant region, Fc region or Fc fragment.

In some instances, a binding moiety can be or include a constant region, Fc region or Fc fragment of an IgG antibody engineered to include an amino acid addition, deletion, or substitution, of one or more of amino acid residues described herein (e.g., 251-256, 285-290, 308-314, 385-389, and 428-436 (Kabat numbering (Kabat et al., (1991) Sequences of Proteins of Immunological Interest, NIH))).

Producing CD19 Antibodies and Fragments Thereof

In some embodiments, an antibody or fragment thereof described herein is engineered to include one or more binding moieties that exhibit pH sensitive binding to one or more targets by mutagenesis using known techniques. For example, a sequence of a reference polypeptide (e.g., a therapeutic antibody or therapeutic fusion protein) can be obtained, and one or more amino acid residues can be added, deleted, or substituted. In some embodiments, one or more amino acid residues are substituted with histidine, arginine, lysine, aspartic acid, glutamic acid, serine, threonine, asparagine, or glutamine. In some embodiments, one or more amino acids are substituted with histidine. Without wishing to be bound by theory, it is believed that substitution of an amino acid residue with a histidine results in insertion of a protonation site, which can increase pH sensitivity of a binding moiety. Polypeptides can be produced using standard methods and assayed for binding to targets of interest as described herein. Additional methods of increasing pH sensitivity of a binding moiety are described in, e.g., Sarkar et al., Nature Biotechnology 20:908-913 (2002); Murtaugh et al., Protein Science 20:1619-1631 (2011); and U.S. Publ. No. 20110229489.

In some embodiments, a first target of interest is selected, and an antibody that selectively binds to the target is provided, obtained, and/or produced (e.g., using known methods as described herein). One or more amino acids of an antigen-binding region and/or an Fc region are substituted (e.g., with histidine, arginine, lysine, aspartic acid, glutamic acid, serine, threonine, asparagine, or glutamine), and pH sensitivity of binding to the target (and, additionally or alternatively, to FcRn) is determined.

In some embodiments, a polypeptide that naturally binds to a target of interest is provided, obtained, and/or produced. The polypeptide is conjugated to an Fc region or Fc fragment described herein (e.g., which binds to FcRn with a desired binding affinity) using known methods. For example, the polypeptide and Fc region or Fc fragment can be conjugated by chemical means or by recombinant expression as a fusion protein. Additionally or alternatively, one or more amino acids of the polypeptide can be substituted (e.g., with histidine, arginine, lysine, aspartic acid, glutamic acid, serine, threonine, asparagine, or glutamine), and pH sensitivity of binding of the polypeptide and the target is determined.

In some embodiments, an antibody or fragment thereof described herein is engineered to include one or more binding moieties identified and/or selected by screening. For example, an antigen-binding moiety that binds antigen in a pH sensitive manner can be identified using a library, e.g., a phage library, expressing antigen-binding moieties. Such a library can be screened for antigen-binding moieties that have a first affinity for antigen at a first pH (e.g., at pH 7.4) and that have a second affinity for antigen at a second pH (e.g., at pH 5.5). An antibody or fragment thereof described herein can be engineered to include such identified pH-sensitive antigen-binding moieties. Additionally and/or alternatively, an FcRn-binding moiety that binds FcRn in a pH sensitive manner can be identified using a library. Methods of screening recombinant antibody libraries are known (see, e.g., Hoogenboom, Nature Biotech. 23:1105-1116 (2005); U.S. Pat. Nos. 5,837,500; 5,571,698; WO 2012/044831).

PEGylation

In certain embodiments, an anti-CD19 antibody as described herein can be PEGylated to include mono- or poly-(e.g., 2-4) PEG moieties. Such PEGylated antibodies may display increased half-life in comparison to a non-PEGylated reference antibody, e.g., an antibody having the same amino acid sequence but different, a different amount of, or no PEGylation.

PEGylation can be carried out by any suitable reaction known in the art. Methods for preparing a PEGylated protein can generally include (a) reacting a polypeptide with polyethylene glycol (such as a reactive ester or aldehyde derivative of PEG) under conditions whereby the polypeptide becomes attached to one or more PEG groups; and (b) obtaining the reaction product(s). In general, the conditions for the reactions can be determined case by case based on known parameters and the desired result.

There are a number of PEG attachment methods available to those skilled in the art. For example, the step of PEGylating an antibody or fragment thereof described herein can be carried out via an acylation reaction or an alkylation reaction with a reactive polyethylene glycol molecule.

Measuring Interactions of Binding Moieties and Targets

The binding properties of an antibody or fragment thereof described herein (e.g., an anti-CD19 antibody described herein) to a target (e.g., CD19 and/or FcRn) can be measured by methods known in the art, e.g., one of the following methods: BIACORE® analysis, Enzyme Linked Immunosorbent Assay (ELISA), x-ray crystallography, sequence analysis and scanning mutagenesis. The binding interaction of an antibody and CD19 and/or FcRn can be analyzed using surface plasmon resonance (SPR). SPR or Biomolecular Interaction Analysis (BIA) detects bio-specific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden). Additionally, a KinExA® (Kinetic Exclusion Assay) assay, available from Sapidyne Instruments (Boise, Id.) can also be used.

Information from SPR can be used to provide an accurate and quantitative measure of the equilibrium dissociation constant ($K_D$), and kinetic parameters, including $K_{on}$ and $K_{off}$, for the binding of a binding moiety to a target (e.g., an anti-CD19 antibody to CD19 and/or FcRn). Such data can be used to compare different molecules. Information from SPR can also be used to develop structure-activity relationships (SAR). For example, the kinetic and equilibrium binding parameters of particular binding moieties to targets at various pH levels can be evaluated. Variant amino acids at given positions can be identified that correlate with particular binding parameters, e.g., high affinity, low affinity, and slow $K_{off}$, at particular pH levels.

Methods of Treatment

In some embodiments, an antibody or fragment thereof described herein (e.g., an anti-CD19 antibody as described herein) is used in a method of treating one or more CD19-associated conditions. In some embodiments, an antibody or fragment thereof described herein (e.g. an anti-CD19 antibody as described herein) is for use as a medicament. CD19-associated conditions can include, without limitation, conditions that are caused by, include, include symptoms resulting in whole or in part from, or are known to occur in conjunction with CD19 expression.

In some aspects, the present invention provides a method for treating a cancer comprising administering an agent that specifically binds CD19 (e.g. an anti-CD19 antibody described herein or fragment thereof). A cancer is a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. In some embodiments, the "cancer" or "cancer tissue" comprises a solid tumor. Examples of cancers that can be treated by the methods of the present invention include, but are not limited to, cancers of the immune system including lymphoma, leukemia, myeloma, and other leukocyte malignancies. In some embodiments, the cancer is a B-cell lymphoma.

In some embodiments, the B-cell lymphoma is selected from the group consisting of Acute Lymphoblastic Leukemia (ALL), AIDS-related lymphoma, ALK-positive large B-cell lymphoma, Burkitt's lymphoma, Chronic lymphocytic leukemia (CLL), Classical Hodgkin lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia. In some embodiments, the B-cell lymphoma is selected from the group consisting of Acute Lymphoblastic Leukemia (ALL), Chronic lymphocytic leukemia, CLL), Diffuse large B-cell lymphoma (DLBCL), Follicular lymphoma, Mantle cell lymphoma (MCL), Marginal zone B-cell lymphoma (MZL), Mucosa-Associated Lymphatic Tissue lymphoma (MALT), and Non-Hodgkin's lymphoma. In some embodiments, the B-cell lymphoma is Non-Hodgkin's lymphoma.

In various embodiments, administration of an antibody or fragment thereof described herein (e.g., an anti-CD19 antibody described herein or fragment thereof) results in a decrease in the prevalence, frequency, level, and/or amount of one or more symptoms or biomarkers of a CD19-associated condition as described herein or otherwise known in the art, e.g., a decrease of at least 3%, 4%, 5%, 6%, 7%, 8%, 9%, 10%, 15%, 20%, 25%, 30%, 35%, 40%, 45%, 50%, 60%, 70%, 80%, 90%, 95%, 99%, or 100% of one or more symptoms or biomarkers as compared to a prior measurement in the subject or to a reference value.

In some embodiments, administration of an antibody or fragment thereof described herein (e.g., an anti-CD19 antibody described herein) to a subject having cancer results in a greater decrease or improvement in one or more symptoms or biomarkers of cancer than does a reference antibody e.g., an antibody that cross-competes for CD19 binding, under comparable conditions In some embodiments, an antibody or fragment thereof described herein (e.g., an anti-CD19 antibody as described herein) exhibits a decreased effective dose as compared to a reference protein (e.g., an antibody that cross-competes for CD19 binding). For instance, an effective dose of an anti-CD19 antibody as described herein may be, e.g., less than 1,000 mg/dose, e.g., less than 900 mg/dose, 800 mg/dose, 700 mg/dose, 600 mg/dose, 500 mg/dose, 550 mg/dose, 400 mg/dose, 350 mg/dose, 300 mg/dose, 200 mg/dose, 100 mg/dose, 50 mg/dose, 25 mg/dose, or less. In certain instances, an effective dose of an anti-CD19 antibody as disclosed herein is lower than an effective or recommended or approved dosage of a reference antibody, which dosage of a reference antibody may be, e.g., 900 mg/dose or 600 mg/dose. Alternatively or in combination with a dosage as disclosed herein, an anti-CD19 antibody as described herein may be effectively or usefully administered at a frequency that is less than once per week, e.g., less than once every week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months, 7 months, 8 months, 9 months, 10 months, 11 months, or year. In certain instances, an effective or useful administration frequency of an anti-CD19 antibody as disclosed herein is lower than an effective or recommended or approved administration frequency of a reference antibody, which administration frequency can be administered weekly (e.g., at a dosage of 300-600 mg, depending on weight of subject) or every two weeks (e.g., at a dosage of 300-1200 mg, depending on weight of subject).

In some embodiments, an antibody or fragment thereof described herein (e.g., an anti-CD19 antibody described herein) can be administered at a decreased dose amount as compared to a reference protein, e.g., an antibody that cross-competes for CD19 binding, while achieving an equal, equally effective, comparably effective, or substantially effective outcome, where the anti-CD19 antibody is administered in an identical, equivalent, or substantially equivalent formulation and/or by an identical, equivalent, or substantially equivalent route of administration as the reference (e.g., an antibody that cross-competes for CD19 binding). In some embodiments, an anti-CD19 antibody described herein can be administered at an increased interval as compared to a reference antibody (e.g., an antibody that cross-competes for CD19 binding) while achieving an equal, equally effective, comparably effective, or substantially effective outcome, where the anti-CD19 antibody is administered in an identical, equivalent, or substantially equivalent formulation and/or by an identical, equivalent, or substantially equivalent route of administration as the reference. In some embodiments, an anti-CD19 antibody described herein can be administered in a decreased number of unit dosages, and/or for a decreased period of treatment, as compared to a reference antibody while achieving an equal, equally effective, comparably effective, or substantially effective outcome, where the anti-CD19 antibody is administered in an identical, equivalent, or substantially equivalent formulation and/or by an identical, equivalent, or substantially equivalent route of administration as the reference (e.g., an antibody that cross-competes for CD19 binding).

In accordance with some such embodiments, an administered dose of an anti-CD19 antibody described herein may be less likely to elicit an adverse response when administered to a subject, e.g., an adverse immune response, than would an effective dose of a reference antibody, e.g., e.g., an antibody that cross-competes for CD19 binding. Accordingly, in various embodiments, an anti-CD19 antibody as disclosed herein may be less likely than a reference antibody, per unit of activity administered to induce an adverse reaction or side effect. In various embodiments, an anti-CD19 antibody as disclosed herein may less likely than a reference antibody, per unit of activity administered, to induce an adverse reaction or side effect having a particular degree of severity. In various embodiments, an anti-CD19 antibody as disclosed herein may induce one or more adverse reactions or side effects to a lesser degree or in fewer patients than a reference antibody, per unit of activity administered. Examples of adverse reactions or side effects that may be associated with the administration of an antibody capable of binding CD19, may include headache, nasopharyngitis, back pain, nausea, diarrhea, hypertension, upper respiratory infection, abdominal pain, vomiting, anemia, cough, peripheral edema, and/or urinary tract infection.

In some embodiments, upon administration to a subject (e.g., at a single dose), an antibody or fragment thereof described herein (e.g., an anti-CD19 antibody described herein) is measured at an increased level in plasma at a defined time following administration (e.g., 1, 2, 3, 4, 5, 6, 7, 8, 9, 10, 11, 12, 13, 14, or more days), relative to level of a control at the same defined time (e.g., an antibody that cross-competes for CD19 binding). For example, at a defined time following administration of a single dose, a level of an anti-CD19 antibody described herein is at least 10%, 20%, 30%, 40%, 50%, 60%, 70%, 80%, 90%, 100%, 150%, 200%, 300%, 400%, or 500% higher than a corresponding level of a reference antibody.

In some embodiments, an antibody or fragment thereof described herein (e.g., an anti-CD19 antibody described herein) is measured at an increased level in plasma at a defined time (e.g., 1, 2, 3, 4, 5, 6, 7, 8, 9, 10, 11, 12, 13, 14, or more days) following administration (e.g., of a single dose), relative to level of a control at the same defined time. For example, at a defined time following administration, a level of an anti-CD19 antibody described herein is at least 10%, 20%, 30%, 40%, 50%, 60%, 70%, 80%, 90%, 100%, 150%, 200%, 300%, 400%, or 500% higher than a corresponding level of a reference antibody.

In some embodiments, an anti-CD19 antibody described herein has increased half-life (e.g., relative to a control, e.g., a reference antibody, e.g., an antibody that cross-competes for CD19 binding), and thus the anti-CD19 antibody can be administered to a subject at increased inter-dose intervals. For example, an anti-CD19 antibody can be administered once every week, every two weeks, every three weeks, every four weeks, every 6 weeks, every 8 weeks, or longer duration.

In some embodiments, a therapeutically effective amount of an antibody or fragment thereof described herein (e.g., an anti-CD19 antibody described herein) is about 90%, 80%, 70%, 60%, 50%, 40%, 30%, 20%, 10%, or 5% of an effective amount of a reference therapeutic protein, e.g., an antibody that cross-competes for CD19 binding). In some embodiments, a single dose of an anti-CD19 antibody described herein achieves a comparable therapeutic effect as two or more doses of a reference antibody.

In some embodiments, an antibody or fragment thereof described herein (e.g., an anti-CD19 antibody described herein) is administered at a dose that is about 90%, 80%, 70%, 60%, 50%, 40%, 30%, 20%, 10%, or 5% of the concentration of a target antigen (e.g., CD19) in the subject.

In some embodiments, an antibody or fragment thereof described herein (e.g., an anti-CD19 antibody described herein) can be physical introduced to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, including a topical, epidermal or mucosal route of administration, for example, intranasally, vaginally, rectally, sublingually or topically. Administering can also be performed, for example, once, a plurality of times, and/or over one or more extended periods.

In some embodiments, an antibody or fragment thereof described herein (e.g., an anti-CD19 antibody described herein) can be used in a number of diagnostic and therapeutic applications. For example, detectably-labeled versions of engineered antibodies as described herein can be used in assays to detect the presence or amount of the CD19 in a sample (e.g., a biological sample). Engineered antibodies described herein can be used in in vitro assays for studying binding to CD19. In some embodiments, an anti-CD19 antibody described herein can be used as a positive control in an assay designed to identify additional novel compounds that are otherwise are useful for treating a CD19-associated disorder. For example, an anti-CD19 antibody described herein can be used as a positive control in an assay to identify additional compounds (e.g., small molecules, aptamers, or antibodies) that bind to CD19.

The antibodies or antigen-binding fragments thereof described herein may be used in monitoring a subject, e.g., a subject having, suspected of having, at risk of developing, or under treatment for one or more CD19-associated conditions. Monitoring may include determining the amount or activity of CD19 in a subject, e.g., in the serum of a subject. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration of an anti-CD19 antibody as described herein. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a CD19-associated disorder described herein.

Formulations and Administration

In various embodiments, antibodies or antigen-binding fragments thereof described herein (e.g., an anti-CD19 antibody described herein) can be incorporated into a pharmaceutical composition. Such a pharmaceutical composition can be useful, e.g., for the prevention and/or treatment of diseases, e.g., a CD19-associated disorder. Pharmaceutical compositions can be formulated by methods known to those skilled in the art (such as described in Remington's Pharmaceutical Sciences, 17th edition, ed. Alfonso R. Gennaro, Mack Publishing Company, Easton, Pa. (1985)).

A suitable means of administration can be selected based on the age and condition of a subject. A single dose of the pharmaceutical composition containing an antibody or fragment thereof described herein (e.g., an anti-CD19 antibody described herein) can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

In various embodiments, a pharmaceutical composition can be formulated to include a pharmaceutically acceptable carrier or excipient. Examples of pharmaceutically acceptable carriers include, without limitation, any and all solvents, dispersion media, coatings, antibacterial and antifungal agents, isotonic and absorption delaying agents, and the like that are physiologically compatible. Compositions of the present invention can include a pharmaceutically acceptable salt, e.g., an acid addition salt or a base addition salt.

In various embodiments, a composition including an antibody as described herein, e.g., a sterile formulation for injection, can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

As disclosed herein, a pharmaceutical composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

Selection or use of any particular form may depend, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

In various embodiments, a pharmaceutical composition of the present invention can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

A pharmaceutical composition can be administered parenterally in the form of an injectable formulation comprising a sterile solution or suspension in water or another pharmaceutically acceptable liquid. For example, the pharmaceutical composition can be formulated by suitably combining therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided. Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

In particular instances, a pharmaceutical composition can be formulated as a solution. In some embodiments, a composition can be formulated, for example, as a buffered solution at a suitable concentration and suitable for storage at 2-8° C. (e.g., 4° C.).

Compositions including one or more engineered antibodies as described herein can be formulated in immunoliposome compositions. Such formulations can be prepared by methods known in the art. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions can be formulated in a composition suitable for intrapulmonary administration (e.g., for administration via an inhaler or nebulizer) to a mammal such as a human. Methods for formulating such compositions are well known in the art. Dry powder inhaler formulations and suitable systems for administration of the formulations are also known in the art. Pulmonary administration may be oral and/or nasal. Examples of pharmaceutical devices for pulmonary delivery include metered dose inhalers, dry powder inhalers (DPIs), and nebulizers. For example, a composition described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TURBOHALER® (AstraZeneca; London, England) the AIR® inhaler (ALKERMES®; Cambridge, Mass.); ROTAHALER® (GlaxoSmithKline; London, England); and ECLIPSE™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition described herein can be intrapulmonarily administered by way of a metered dose inhaler. These inhalers rely on a propellant to deliver a discrete dose of a compound to the lungs. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, compositions can be formulated for delivery to the eye, e.g., in the form of a pharmaceutically acceptable solution, suspension or ointment. A preparation for use in treating an eye can be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents. A preparation as described herein can be administered topically to the eye of the subject in need of treatment (e.g., a subject afflicted with AMD) by conventional methods, e.g., in the form of drops, or by bathing the eye in a therapeutic solution, containing one or more compositions.

A variety of devices for introducing drugs into the vitreal cavity of the eye may be appropriate, in certain embodiments, for administration of a composition as described herein. For example, U.S. Publication No. 2002/0026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. Additional methods and devices (e.g., a transscleral patch and delivery via contact lenses) for delivery of a therapeutic agent to the eye are described in, e.g., Ambati and Adamis (2002) *Prog Retin Eye Res* 21(2): 145-151; Ranta and Urtti (2006) *Adv Drug Delivery Rev* 58(11):1164-1181; Barocas and Balachandran (2008) *Expert Opin Drug Delivery* 5(1): 1-10(10); Gulsen and Chauhan (2004) *Invest Opthalmol Vis Sci* 45:2342-2347; Kim et al. (2007) *Ophthalmic Res* 39:244-254; and PCT publication no. WO 04/073551, the disclosures of which are incorporated herein by reference in their entirety.

In certain embodiments, administration of an antibody as described herein is achieved by administering to a subject a nucleic acid encoding the antibody. Nucleic acids encoding a therapeutic antibody described herein can be incorporated into a gene construct to be used as a part of a gene therapy protocol to deliver nucleic acids that can be used to express and produce antibody within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407). Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci* USA 85:6460-6464; Wilson et al. (1988) *Proc Natl Acad Sci USA* 85:3014-3018; Armentano et al. (1990) *Proc Natl Acad Sci USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immuno/*150:4104-4115; U.S. Pat. Nos. 4,868,116 and 4,980,286; and PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) (el/68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and Mclaughlin et al. (1989) *J Virol* 62:1963-1973.

In various embodiments, subcutaneous administration can be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with antibody drug for subcutaneous injection.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering solution to a subject with as little pain as possible. One medication delivery pen includes a vial holder into which a vial of a therapeutic or other medication may be received. The pen may be an entirely mechanical device or it may be combined with electronic circuitry to accurately set and/or indicate the dosage of medication that is injected into the user. See, e.g., U.S. Pat. No. 6,192,891. In some embodiments, the needle of the pen device is disposable and the kits include one or more disposable replacement needles. Pen devices suitable for delivery of any one of the presently featured compositions are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, MOLLY™, manufactured by Scandinavian Health Ltd.

In some embodiments, a composition described herein can be therapeutically delivered to a subject by way of local administration. As used herein, "local administration" or "local delivery," can refer to delivery that does not rely upon transport of the composition or agent to its intended target tissue or site via the vascular system. For example, the composition may be delivered by injection or implantation of the composition or agent or by injection or implantation of a device containing the composition or agent. In certain embodiments, following local administration in the vicinity of a target tissue or site, the composition or agent, or one or more components thereof, may diffuse to an intended target tissue or site that is not the site of administration.

In some embodiments, the compositions provided herein are present in unit dosage form, which unit dosage form can be suitable for self-administration. Such a unit dosage form may be provided within a container, typically, for example, a vial, cartridge, prefilled syringe or disposable pen. A doser such as the doser device described in U.S. Pat. No. 6,302,855, may also be used, for example, with an injection system as described herein.

A suitable dose of a composition described herein, which dose is capable of treating or preventing a disorder in a subject, can depend on a variety of factors including, e.g., the age, sex, and weight of a subject to be treated and the particular inhibitor compound used. For example, a different dose of one composition including an antibody as described herein may be required to treat a subject with a CD19-associated disorder as compared to the dose of a different formulation of that antibody. Other factors affecting the dose administered to the subject include, e.g., the type or severity of the disorder. For example, a subject having one CD19-associated disorder may require administration of a different dosage than a subject with another CD19-associated disorder. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject may also be adjusted based upon the judgment of the treating medical practitioner.

A composition described herein can be administered as a fixed dose, or in a milligram per kilogram (mg/kg) dose. In some embodiments, the dose can also be chosen to reduce or avoid production of antibodies or other host immune responses against one or more of the antibody or an antigen-binding fragment thereof in the composition. While in no way intended to be limiting, exemplary dosages of an antibody, such as a composition described herein include, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition described herein include, without limitation, 0.1 mg/kg, 0.5 mg/kg, 1.0 mg/kg, 2.0 mg/kg, 4 mg/kg, 8 mg/kg, or 20 mg/kg.

A pharmaceutical solution can include a therapeutically effective amount of a composition described herein. Such effective amounts can be readily determined by one of ordinary skill in the art based, in part, on the effect of the administered composition, or the combinatorial effect of the composition and one or more additional active agents, if more than one agent is used. A therapeutically effective amount of a composition described herein can also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the a CD19-associated disorder. For example, a therapeutically effective amount of a composition described herein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by therapeutically beneficial effects.

Suitable human doses of any of the compositions described herein can further be evaluated in, e.g., Phase I dose escalation studies. See, e.g., van Gurp et al. (2008) *Am J Transplantation* 8(8): 1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of compositions can be determined by known pharmaceutical procedures in cell cultures or experimental animals (e.g., animal models of any of the CD19-associated disorders). These procedures can be used, e.g., for determining the $LD_{50}$ (the dose lethal to 50% of the population) and the ED50 (the dose therapeutically effective in 50% of the population). The dose ratio between toxic and therapeutic effects is therapeutic index and it can be expressed as the ratio $LD_{50}$/ED50. A composition described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

Those of skill in the art will appreciate that data obtained from cell culture assays and animal studies can be used in formulating a range of dosage for use in humans. Appropriate dosages of compositions described herein lie generally within a range of circulating concentrations of the compositions that include the ED50 with little or no toxicity. The dosage may vary within this range depending upon the dosage form employed and the route of administration utilized. For a composition described herein, therapeutically effective dose can be estimated initially from cell culture assays. A dose can be formulated in animal models to achieve a circulating plasma concentration range that includes the Io (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

Combination Therapies

In various embodiments, an anti-CD19 antibody as described herein may be included in a course of treatment that further includes administration of at least one additional agent to a subject. In various embodiments, an additional agent administered in combination with an anti-CD19 antibody as described herein may be an agent chemotherapy agent. In various embodiments, an additional agent administered in combination with an antibody as described herein may be an agent that inhibits inflammation.

In some embodiments, the anti-CD19 antibody is a single chain variable fragment (scFv) with specificity for human CD19. In some embodiments, the anti-CD19 scFv can be conjugated (e.g., linked to) to a therapeutic agent (e.g., a chemotherapeutic agent and a radioactive atom) for binding to a cancer cell, delivering therapeutic agent to the cancer cell, and killing the cancer cell which expresses human CD19. In some embodiments, an anti-CD19 antibody is linked to a therapeutic agent. In some embodiments, therapeutic agent is a chemotherapeutic agent, a cytokine, a radioactive atom, an siRNA, or a toxin. In some embodiments, therapeutic agent is a chemotherapeutic agent. In some embodiments, the agent is a radioactive atom.

In some embodiments, the methods can be performed in conjunction with other therapies for CD19-associated disorders. For example, the composition can be administered to a subject at the same time, prior to, or after, chemotherapy. In some embodiments, the composition can be administered to a subject at the same time, prior to, or after, an adoptive therapy method.

In various embodiments, an additional agent administered in combination with an anti-CD19 antibody as described herein may be administered at the same time as an anti-CD19 antibody, on the same day as an anti-CD19 antibody, or in the same week as an anti-CD19 antibody. In various embodiments, an additional agent administered in combination with an anti-CD19 antibody as described herein may be administered in a single formulation with an anti-CD19 antibody. In certain embodiments, an additional agent administered in a manner temporally separated from administration of an anti-CD19 antibody as described herein, e.g., one or more hours before or after, one or more days before or after, one or more weeks before or after, or one or more months before or after administration of an anti-CD19 antibody. In various embodiments, the administration frequency of one or more additional agents may be the same as, similar to, or different from the administration frequency of an anti-CD19 antibody as described herein.

Encompassed within combination therapy is the a treatment regimen that includes administration of two distinct antibodies as described herein and/or a treatment regimen that includes administration of an antibody as described herein by a plurality of formulations and/or routes of administration.

In some embodiments, compositions can be formulated with one or more additional therapeutic agents, e.g., additional therapies for treating or preventing a CD19-associated disorder (e.g., a cancer or autoimmune disorder) in a subject. Additional agents for treating a CD19-associated disorder in a subject will vary depending on the particular disorder being treated, but can include, without limitation, rituximab, cyclophosphamide, doxorubicin, vincristine, prednisone, osfamide, carboplatin, etoposide, dexamethasone, cytarabine, cisplatin, cyclophosphamide, or fludarabine.

A composition described herein can replace or augment a previously or currently administered therapy. For example, upon treating with a composition described herein, administration of the one or more additional active agents can cease or diminish, e.g., be administered at lower levels, e.g., lower levels of a reference antibody that cross-competes for CD19 binding) following administration of an anti-CD19 antibody described herein. In some embodiments, administration of the previous therapy can be maintained. In some embodiments, a previous therapy will be maintained until the level of the composition reaches a level sufficient to provide a therapeutic effect. The two therapies can be administered in combination.

Recombinant Gene Technology

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Recombinant expression of a gene, such as a nucleic acid encoding a polypeptide, such as an anti-CD19 antibody described herein, can include construction of an expression vector containing a nucleic acid that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured by conventional techniques to produce polypeptides.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

EXAMPLES

The following examples describe some of the preferred modes of making and practicing the present invention. However, it should be understood that these examples are for illustrative purposes only and are not meant to limit the scope of the invention.

Example 1. Identification and Characterization of Anti-CD19 Antibodies

The present Example demonstrates characterization of anti-CD19 antibodies. Human anti-CD19 antibodies were derived from and produced in Adimab yeast. Antigens were biotinylated using the EZ-Link™ Sulfo-NHS-Biotinylation Kit (Thermo Scientific, Cat #21425). The antigens were concentrated to about 1 mg/mL and buffer exchanged into PBS before addition of 1:7.5 molar ratio of biotinylation reagent. The mixture was held at 4C overnight prior to another buffer exchange to remove free biotin in the solution. Biotinylation was confirmed through streptavidin sensor binding of the labeled proteins on a ForteBio.

Eight naïve human synthetic yeast libraries each of ~$10^9$ diversity were propagated as previously described (see, e.g., Y. Xu et al, PEDS 26(10), 663-70 (2013); WO2009036379; WO2010105256; and WO2012009568.)

For the first two rounds of selection, a magnetic bead sorting technique utilizing the Miltenyi MACS system was performed, as previously described (see, e.g., Siegel et al, J Immunol Methods 286(1-2), 141-153 (2004).) Briefly, yeast cells (~1010 cells/library) were incubated with biotinylated antigen for 30 min at 30° C. in wash buffer (phosphate-buffered saline (PBS)/0.1% bovine serum albumin (BSA)). After washing once with 40 mL ice-cold wash buffer, the cell pellet was resuspended in 20 mL wash buffer, and Streptavidin MicroBeads (500 µl) were added to the yeast and incubated for 15 min at 4° C. Next the yeast were pelleted, resuspended in 5 mL wash buffer, and loaded onto a Miltenyi LS column. After the 5 mL were loaded, the column was washed 3 times with 3 mL wash buffer. The column was then removed from the magnetic field, and the yeast were eluted with 5 mL of growth media and then grown overnight.

The third round of selection was performed using flow cytometry (FACS). Approximately $2\times10^7$ yeast were pelleted, washed three times with wash buffer, and incubated at 30° C. with 100-200 nM biotinylated antigen under equilibrium conditions. The fourth and fifth rounds of selections were performed by incubating biotinylated NALM-6 and Raji cells with the selected yeast output from the round 3 FACS. After incubation, pre-washed M-280 Strepavidin Dynabeads® (Cat #60210) were added to the yeast/mammalian cell complexes and incubated. Next, the complexes were separated using a DynaMag™-2 magnet and the non-binding supernatants were removed. The bead/cell complexes were washed three times with 1 mL of selection buffer. The captured complexes were then transferred into flasks containing yeast growth media for propagation. In the sixth round of selection, propagated yeast were subjected to either an additional round of NALM-6/Raji cell selection, selection with 100 nM recombinant CD19 antigen, or negative selection with a polyspecificity reagent (PSR) to remove non-specific antibodies.

For the PSR depletion, the libraries were incubated with a 1:10 dilution of biotinylated PSR reagent as previously described (see, e.g., Y. Xu et al, PEDS 26(10), 663-70 (2013).) Yeast were then washed twice with wash buffer and stained with goat F(ab')$_2$ anti-human kappa-FITC (LC-FITC) diluted 1:100 (Southern Biotech, Cat #2062-02) and either Streptavidin-AF633 (SA-633) diluted 1:500 (Life Technologies, Cat #S21375) or Extravidin®-phycoerthyrin (EA-PE) diluted 1:50 (Sigma-Aldrich, Cat #E4011), secondary reagents for 15 min at 4° C. After washing twice with ice-cold wash buffer, the cell pellets were resuspended in 0.3 mL wash buffer and transferred to strainer-capped sort tubes. Sorting was performed using a FACSAria™ sorter (BD Biosciences) and sort gates were determined to select for antibodies with desired characteristics. Selection rounds were repeated until a population with all of the desired characteristics was obtained. After the final round of sorting, yeast were plated and individual colonies were picked for characterization.

Light Chain Diversification

Heavy chains from the naïve output were used to prepare light chain diversification libraries used for additional selection rounds. Heavy chain plasmids were extracted from the yeast, propagated in and subsequently purified from E. coli, and transformed into a light chain library with a diversity of $5\times10^6$. Selections were performed on these libraries as described above, i.e., with one round of MACS, two rounds of cell selection with either Raji or NALM-6 cells, followed by a fourth round FACS selection using recombinant CD19 antigen. Specific to the light chain diversification, the Raji and NALM-6 cells selections incorporated an initial negative selection with engineered Raji and NALM-6 cells that had undergone targeted genetic knockout of the CD19 gene. Following the depletion with the CD19 knockout cells, a positive selection was performed using engineered Raji and NALM-6 cells that expressed both endogenous CD19 and overexpressed. In the different FACS selection rounds, the libraries were evaluated for (Poly-Specificity Reagent) PSR binding, species cross-reactivity, and affinity pressure by antigen titration. Sorting was performed in order to obtain a population with the desired characteristics. Individual colonies from each FACS selection round described above were picked for sequencing and characterization.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. ForteBio $K_D$ measurements These anti-CD19 antibodies were tested for their binding affinity on soluble CD19 in a ForteBio Octet® system (Octet® RED384 generally as previously described (see, e.g., Estep et al, Mabs 5(2), 270-278 (2013)). Briefly, ForteBio affinity measurements were performed by loading IgGs on-line onto AHC sensors. The antibodies were immobilized on anti-human IgG pins and bound to soluble CD19-HSA fusion protein (CD19 extracellular domains fused to human serum albumin). Sensors were equilibrated off-line in assay buffer for 30 min and then monitored on-line for 60 seconds for baseline establishment. Sensors with loaded IgGs were exposed to 100 nM soluble CD19-HSA fusion protein antigen for 3 minutes, and afterwards were transferred to assay buffer for 3 min for off-rate measurement. All kinetics were analyzed using the 1:1 binding model. A summary of the binding kinetics are provided in Table 3. The affinities of exemplary antibodies ranged between 8 nM and 20 nM. The vH of all anti-CD19 antibodies shown in Table 3 include a vH sequence of SEQ ID NO: 5.

TABLE 3

Binding kinetics of anti-CD19 antibodies

| CD19 Antibody | vL SEQ ID NO | IgG $K_D$ (M) monovalent | kon (1/Ms) | koff (1/s) |
|---|---|---|---|---|
| Antibody 2 | 20 | 9.01E−09 | 6.15E+04 | 5.54E−04 |
| Antibody 4 | 21 | 9.27E−09 | 2.35E+04 | 2.18E−04 |
| Antibody 5 | 22 | 1.04E−08 | 7.56E+04 | 7.85E−04 |
| Antibody 8 | 23 | 8.22E−09 | 5.52E+04 | 4.54E−04 |
| Antibody 6 | 24 | 6.40E−09 | 7.56E+04 | 4.84E−04 |
| Antibody 7 | 25 | 1.49E−08 | 7.00E+04 | 1.05E−03 |
| Antibody 1 | 26 | 3.29E−08 | 5.34E+04 | 1.76E−03 |
| Antibody 15 | 27 | 2.08E−08 | 6.98E+04 | 1.45E−03 |

Example 2. On-Cell Binding of Anti-CD19 Antibodies

The on-cell binding for the anti-CD19 antibodies were assessed by flow cytometry on the endogenous CD19 expressing Raji and NALM-6 cell lines. Each antibody was tested on both the CD19 positive parental lines and corresponding CD19 knock-out Raji and NALM-6 lines to confirm on-cell target specific binding. The flow cytometry chromatograms shown in FIG. 1 demonstrate 1-2 log shifts on the CD19 positive lines over the background binding on the corresponding knockout cell lines.

Figures 2A, 2B, 2C:
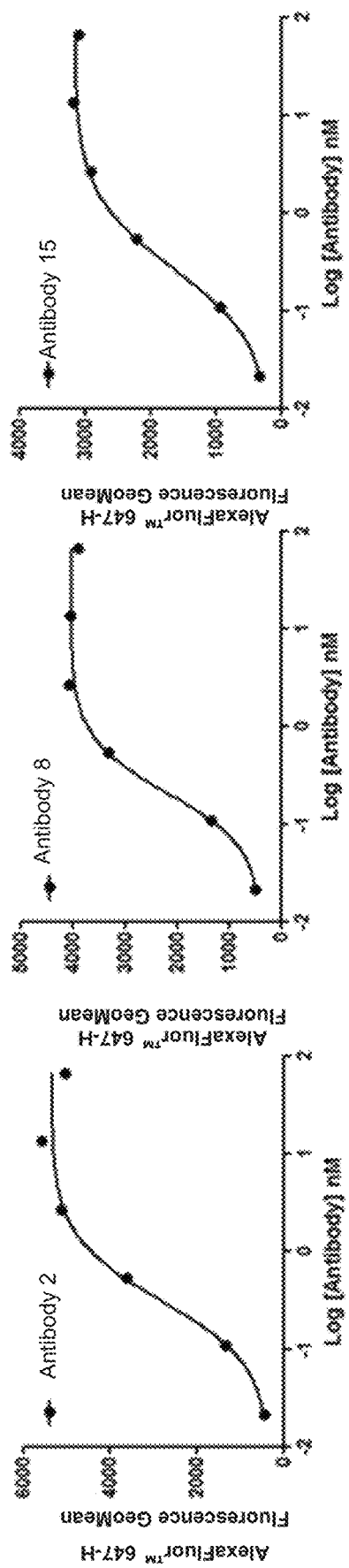
FIG. 2A-2C shows exemplary binding curves of anti-CD19 antibodies binding CD19 on NALM-6 cells.

The serial dilution flow cytometry results shown in FIG. 2A-2C demonstrate saturation binding on NALM-6 cells. The EC50 values calculated from the curves, are provided in Table 4. Exemplary anti-CD19 antibodies bind CD19 positive NALM-6 cells at high affinities from of at least 0.2 nM. The higher affinities observed on CD19 positive cells versus the soluble protein suggests that these antibodies bind an epitope that may be more natively presented on cells than in the CD19-HSA fusion protein.

TABLE 4

EC50 of anti-CD19 antibodies on NALM6 cells

| CD 19 Antibody | vL SEQ ID NO | NALM-6 on-cell binding affinity EC50 (nM) |
|---|---|---|
| Antibody 2 | 20 | 0.3136 |
| Antibody 4 | 21 | 0.5195 |
| Antibody 5 | 22 | 0.2192 |
| Antibody 8 | 23 | 0.2097 |
| Antibody 6 | 24 | 0.1798 |
| Antibody 7 | 25 | 0.2104 |
| Antibody 1 | 26 | 0.5879 |
| Antibody 15 | 27 | 0.2698 |

Example 3. Epitope Binning by Cross Competition

A cross competition epitope binning assay was performed to determine if any of the anti-CD19 antibodies bound a unique, non-competing epitope from a reference anti-CD19 antibody, Denintuzumab. Epitope binning/ligand blocking was performed using a sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Additional binding by the second antibody or ligand after antigen association indicates an unoccupied epitope (non-competitor), while no binding indicates epitope blocking (competitor or ligand blocking).

Figure 3:
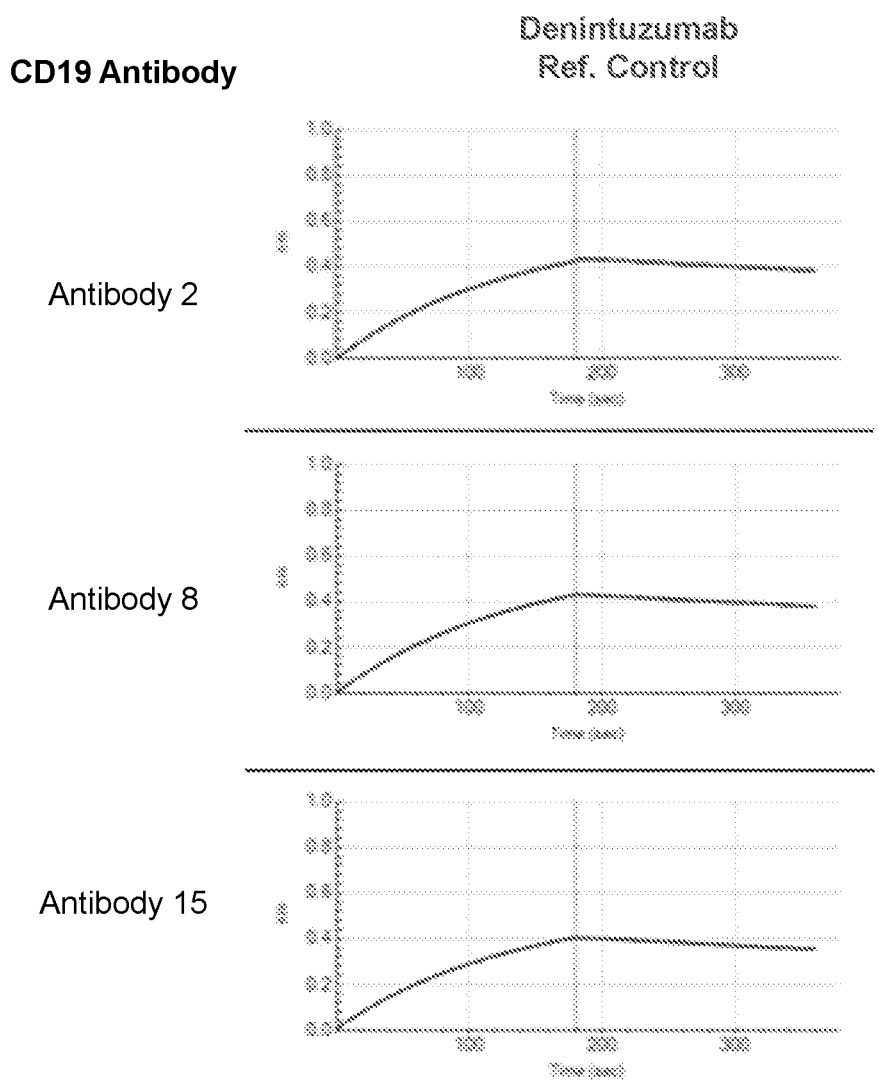
FIG. 3 shows a exemplary results of a competition assay used to characterize anti-CD19 antibodies and antigen binding fragments thereof by epitope binning.

The anti-CD19 reference control Denintuzumab was captured on anti-human IgG pins and then loaded with soluble CD19 in the fluid phase. Instead of performing a dissociation step, a second loading was performed with each of the test antibodies. Those antibodies which bind a non-competing epitope from Denintuzumab would reflect a new binding event on the trace while antibodies with the same epitope are blocked by Denintuzumab reflected by a flat trace. The results shown in FIG. 3 demonstrate that each of antibodies bind epitiopes that compete with Denintuzumab. These results suggest that the antibodies bind a similar epitope on CD19 that competes with the reference anti-CD19 antibody Denintuzumab.

Example 4. Characterization of CD19 Binding of Anti-CD19 scFv

Relative competition for the common epitope was assessed in a Biacore® SPR assay. In this assay, an scFv comprising the vH and vL of the anti-CD19 antibody 2 (SEQ ID NO: 42), was evaluated for relative competition binding to CD19-T2 binder, SJ25cl, and FMC63 (from Kymriah® "Tisagenlecleucel" and Yescarta® "Axicabtagene ciloleucel"). The antibody 2 scFv was immobilized on the Biacore® CM5 chip, which was then bound by a mixture of 100 nM CD19-HSA-his and a titration of each competitor scFv (0, 50 nM, 100 nM, 200 nM, and 800 nM). After a 3 minute competitive binding step, a 5 minute dissociation was performed in buffer HBS-EP (300 mM NaCl).

The CD19 antibody 1 scFv competes with all of the reference antibodies in this assay (data not shown). The FMC63 scFv fully competed for CD19 binding even at the lowest concentration (50 nM). The assay was repeated to include 25 nM where a small amount of binding to CD19 was preserved, suggesting these antibodies bind CD19 with a similar, but slightly higher affinity than the SJ25C1 scFv. These data suggest that all of the binders tested compete for binding to an overlapping epitope on CD19.

To further assess the potential for the anti-CD19 antibodies to bind non-specific membrane proteins, scFvs derived from the CD19 antibodies described herein were evaluated in a surface membrane protein (SMP) assay. The SMP assay is an ELISA based assay with either human HEK-293 or insect SF9 cell membranes coated on the plate to test for non-specific binding to these membranes by the test antibodies. Similar to the SPR assay, internal control high and low non-specific binding antibodies (high non-specific binding control, sc209 and low non-specific binding control, 5f9) were included. The results given were consistent with the SPR assay described above with low binding activity for the CD19 antibodies on either HEK-293 or SF9 membranes.

OTHER EMBODIMENTS

While a number of embodiments of this invention are described herein, the present disclosure and examples may be altered to provide other methods and compositions of this invention. Therefore, it will be appreciated that the scope of this invention is to be defined by the appended claims in addition to the specific embodiments that have been represented by way of example. All references cited herein are hereby incorporated by reference.

The invention claimed is:

1. A CD19 antibody or antigen-binding fragment thereof, comprising:
   (a) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVSSSYLA (SEQ ID NO: 7) (LCDR1), GASSRAT (SEQ ID NO: 9) (LCDR2), and QQAGAVPIT (SEQ ID NO: 12) (LCDR3); or
   (b) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVSSSYLA (SEQ ID NO: 7) (LCDR1), GASSRAT (SEQ ID NO: 9) (LCDR2), and QQVDSLHPFT (SEQ ID NO: 13) (LCDR3); or
   (c) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPLT (SEQ ID NO: 14) (LCDR3); or
   (d) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVRSSYLA (SEQ ID NO: 8) (LCDR1), GASSRAT (SEQ ID NO: 9) (LCDR2), and QQLFDSPYT (SEQ ID NO: 15) (LCDR3); or
   (e) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVRSSYLA (SEQ ID NO: 8) (LCDR1), GASSRAT (SEQ ID NO: 9) (LCDR2), and QQAGVPPLT (SEQ ID NO: 16) (LCDR3); or
   (f) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPFT (SEQ ID NO: 17) (LCDR3); or
   (g) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVSSSYLA (SEQ ID NO: 7) (LCDR1), GASNRAT (SEQ ID NO: 10) (LCDR2), and QQAGVFPFT (SEQ ID NO: 18) (LCDR3); or
   (h) a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and
   a light chain variable region with complementarity determining region (CDR) sequences of RASQSVSSSYLA (SEQ ID NO: 7) (LCDR1), GASRRAT (SEQ ID NO: 11) (LCDR2), and QQAGIPPYT (SEQ ID NO: 19) (LCDR3).

2. The CD19 antibody or antigen-binding fragment thereof of claim 1, comprising:
   a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQAGAVPIT (SEQ ID NO: 12) (LCDR3).

3. The CD19 antibody or antigen-binding fragment thereof of claim 1, comprising:

a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQVDSLHPFT (SEQ ID NO: 13) (LCDR3).

4. The CD19 antibody or antigen-binding fragment thereof of claim 1, comprising:

a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPLT (SEQ ID NO: 14) (LCDR3).

5. The CD19 antibody or antigen-binding fragment thereof of claim 1, comprising:

a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVRSSYLA (SEQ ID NO: 8) (LCDR1), GASSRAT (SEQ ID NO: 9) (LCDR2), and QQLFDSPYT (SEQ ID NO: 15) (LCDR3).

6. The CD19 antibody or antigen-binding fragment thereof of claim 1, comprising:

a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVRSSYLA (SEQ ID NO: 8) (LCDR1), GASSRAT (SEQ ID NO: 9) (LCDR2), and QQAGVPPLT (SEQ ID NO: 16) (LCDR3).

7. The CD19 antibody or antigen-binding fragment thereof of claim 1, comprising:

a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASSRAT (SEQ ID NO: 9) (LCDR2), and QQAGGVPPFT (SEQ ID NO: 17) (LCDR3).

8. The CD19 antibody or antigen-binding fragment thereof of claim 1, comprising:

a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASNRAT (SEQ ID NO: 10) (LCDR2), and QQAGVFPFT (SEQ ID NO: 18) (LCDR3).

9. The CD19 antibody or antigen-binding fragment thereof of claim 1, comprising:

a heavy chain variable complementarity determining region (CDR) sequences of SYGMH (SEQ ID NO: 1) (HCDR1), LIWYDGSNKYYADSVKG (SEQ ID NO: 2) (HCDR2) and PVEGLLRGFDY (SEQ ID NO: 3) (HCDR3) and a light chain variable region with complementarity determining region (CDR) sequences of RASQSVSSSYLA (SEQ ID NO: 7) (LCDR1), GASRRAT (SEQ ID NO: 11) (LCDR2), and QQAGIPPYT (SEQ ID NO: 19) (LCDR3).

10. The CD19 antibody or antigen-binding fragment thereof of claim 1, comprising (a) an immunoglobulin light chain variable ($V_L$) region comprising an amino acid sequence that is at least 90% identical to SEQ ID NO: 20; and
an immunoglobulin heavy chain variable ($V_H$) region comprising an amino acid sequence that is at least 90% identical to SEQ ID NO: 5; or (b) an immunoglobulin light chain variable ($V_L$) region comprising an amino acid sequence that is at least 90% identical to SEQ ID NO: 21; and
an immunoglobulin heavy chain variable ($V_H$) region comprising an amino acid sequence that is at least 90% identical to SEQ ID NO: 5; or (c) an immunoglobulin light chain variable ($V_L$) region comprising an amino acid sequence that is at least 90% identical to SEQ ID NO: 22; and
an immunoglobulin heavy chain variable ($V_H$) region comprising an amino acid sequence that is at least 90% identical to SEQ ID NO: 5; or (d) an immunoglobulin light chain variable ($V_L$) region comprising an amino acid sequence that is at least 90% identical to SEQ ID NO: 23; and
an immunoglobulin heavy chain variable ($V_H$) region comprising an amino acid sequence that is at least 90% identical to SEQ ID NO: 5; or (e) an immunoglobulin light chain variable ($V_L$) region comprising an amino acid sequence that is at least 90% identical to SEQ ID NO: 24; and
an immunoglobulin heavy chain variable ($V_H$) region comprising an amino acid sequence that is at least 90% identical to SEQ ID NO: 5; or (f) an immunoglobulin light chain variable ($V_L$) region comprising an amino acid sequence that is at least 90% identical to SEQ ID NO: 25; and
an immunoglobulin heavy chain variable ($V_H$) region comprising an amino acid sequence that is at least 90% identical to SEQ ID NO: 5; or (g) an immunoglobulin light chain variable ($V_L$) region comprising an amino acid sequence that is at least 90% identical to SEQ ID NO: 26; and
an immunoglobulin heavy chain variable ($V_H$) region comprising an amino acid sequence that is at least 90% identical to SEQ ID NO: 5; or (h) an immunoglobulin light chain variable ($V_L$) region comprising an amino acid sequence that is at least 90% identical to SEQ ID NO: 27; and
an immunoglobulin heavy chain variable ($V_H$) region comprising an amino acid sequence that is at least 90% identical to SEQ ID NO: 5.

11. The CD19 antibody or antigen-binding fragment thereof of claim 1, wherein the CD19 antibody or fragment thereof is selected from the group consisting of an IgA antibody, IgG antibody, IgE antibody, IgM antibody, bi- or multi-specific antibody, Fab fragment, Fab' fragment, F(ab')$_2$ fragment, Fd' fragment, Fd fragment, single-chain variable fragment (scFv), polypeptide-Fc fusion, masked antibody, tandem diabody, minibodies, ankyrin repeat protein, TCR-like antibody, and transbody.

12. The CD19 antibody or antigen-binding fragment thereof of claim 1, wherein the CD19 antibody or antigen-binding fragment thereof is a scFv comprising a linker sequence comprising any one of SEQ ID NOs: 36-39.

13. A pharmaceutical composition comprising a CD19 antibody or antigen-binding fragment thereof and a pharmaceutically acceptable carrier, wherein the CD19 antibody or fragment thereof comprises the antibody of claim 1.

14. A nucleic acid sequence encoding one or more polypeptide chains of an anti-CD19 antibody or antigen-binding fragment thereof of claim 10.

15. A vector comprising the nucleic acid sequence of claim 14.

16. An isolated cell comprising the vector of claim 15.

* * * * *